(12) United States Patent
Ariel et al.

(10) Patent No.: US 9,562,893 B2
(45) Date of Patent: Feb. 7, 2017

(54) LACTOFERRIN FRAGMENTS AND USE THEREOF

(71) Applicant: Carmel-Haifa University Economic Corp., Mount Carmel Haifa (IL)

(72) Inventors: Amiram Ariel, Kiryat Motzkin (IL); Aviv Lutaty, Kiryat Ata (IL)

(73) Assignee: CARMEL-HAIFA UNIVERSITY ECONOMIC CORP., Haifa (IL)

( * ) Notice: Subject to any disclaimer, the term of this patent is extended or adjusted under 35 U.S.C. 154(b) by 59 days.

(21) Appl. No.: 14/163,635

(22) Filed: Jan. 24, 2014

(65) Prior Publication Data

US 2014/0162377 A1 Jun. 12, 2014

Related U.S. Application Data

(63) Continuation of application No. PCT/IL2012/050269, filed on Jul. 24, 2012.

(60) Provisional application No. 61/511,056, filed on Jul. 24, 2011.

(51) Int. Cl.

| | |
|---|---|
| *G01N 33/53* | (2006.01) |
| *G01N 27/447* | (2006.01) |
| *C07K 14/79* | (2006.01) |
| *G01N 33/68* | (2006.01) |

(52) U.S. Cl.
CPC .............. *G01N 33/53* (2013.01); *C07K 14/79* (2013.01); *G01N 27/447* (2013.01); *G01N 33/68* (2013.01); *G01N 2333/79* (2013.01); *G01N 2800/52* (2013.01); *G01N 2800/56* (2013.01); *G01N 2800/7095* (2013.01)

(58) Field of Classification Search
None
See application file for complete search history.

(56) References Cited

U.S. PATENT DOCUMENTS

2007/0197426 A1  8/2007  Komine et al.

FOREIGN PATENT DOCUMENTS

| JP | 2003289749 A | 10/2003 |
| JP | 2004155751 A | 6/2004 |
| WO | 0239883 A2 | 5/2002 |

OTHER PUBLICATIONS

Goldman et al., Molecular Forms of Lactoferrin in Stool and Urine from Infants fed Human Milk, Pediatric Research, 27(3), (1990), p. 252-255.*
Bannenberg et al., (2005) Molecular circuits of resolution: formation and actions of resolvins and protectins. J Immunol 174(7): 4345-4355.
Bournazou et al., (2009) Apoptotic human cells inhibit migration of granulocytes via release of lactoferrin. J Clin Invest 119(1): 20-32.
Jesaitis et al., (2003) Compromised host defense on Pseudomonas aeruginosa biofilms: characterization of neutrophil and biofilm interactions. J Immunol 171(8): 4329-4339.
Kanyshkova et al., (2001) Lactoferrin and its biological functions. Biochemistry (Mosc) 66(1):5-13.
Komine et al., (2005) Small molecule lactoferrin with an inflammatory effect but no apparent antibacterial activity in mastitic mammary gland secretion. J Vet Med Sci 67(7): 667-677.
Komine et al., (2006) Effect of combination therapy with lactoferrin and antibiotics against staphylococcal mastitis on drying cows. J Vet Med Sci 68(3): 205-211.
Komine et al., (2006) Inflammatory effect of cleaved bovine lactoferrin by elastase on staphylococcal mastitis. J Vet Med Sci 68(7): 715-723.
Komine et al. (2007) Cleaved inflammatory lactoferrin peptides in parotid saliva of periodontitis patients. Mol Immunol 44(7): 1498-1508.
Schif-Zuck et al., (2011) Saturated-efferocytosis generates pro-resolving CD11b low macrophages: modulation by resolvins and glucocorticoids. Eur J Immunol 41(2): 366-379.
Vogel et al., (2002) Towards a structure-function analysis of bovine lactoferricin and related tryptophan- and arginine-containing peptides. Biochem Cell Biol 80(1): 49-63.
"Datasheet Lactoferrin (H-65): sc-25622", Mar. 18, 2012, p. 1, XP055159360, Retrieved from the Internet: https://web.archive.org/web/20120718055721/http://datasheets.scbt.com/sc-25622.pdf. Retrieved on Dec. 18, 2014.
de la Rosa et al., (2008) Lactoferrin acts as an alarmin to promote the recruitment and activation of APCs and antigen-specific immune responses. J Immunol 180(10): 6868-76.
Serhan (2010) Novel lipid mediators and resolution mechanisms in acute inflammation: to resolve or not? Am J Pathol 177(4): 1576-91.
Thuijls et al., (2011) A pilot study on potential new plasma markers for diagnosis of acute appendicitis. Am J Emerg Med 29(3): 256-60.

* cited by examiner

*Primary Examiner* — Christine Foster
*Assistant Examiner* — Ellen J Marcsisin
(74) *Attorney, Agent, or Firm* — Vorys, Sater, Seymour & Pease LLP

(57) ABSTRACT

Novel lactoferrin fragments that are characteristic of inflammation during resolution and uses thereof. Diagnostic compositions and methods for assessing the presence or absence of resolving inflammation and for monitoring the progression of inflammatory resolution in a subject. Methods for treating a subject having an inflammatory disease, the methods including determining whether the subject has inflammation in resolution by determining the molecular weight of lactoferrin fragments.

5 Claims, 5 Drawing Sheets

SEQUENCE LISTING

```
<160> NUMBER OF SEQ ID NOS: 19

<210> SEQ ID NO 1
<211> LENGTH: 172
<212> TYPE: PRT
<213> ORGANISM: Bos taurus

<400> SEQUENCE: 1

Phe Phe Ser Ala Ser Cys Val Pro Cys Ile Asp Arg Gln Ala Tyr Pro
1               5                   10                  15

Asn Leu Cys Gln Leu Cys Lys Gly Glu Gly Glu Asn Gln Cys Ala Cys
            20                  25                  30

Ser Ser Arg Glu Pro Tyr Phe Gly Tyr Ser Gly Ala Phe Lys Cys Leu
        35                  40                  45

Gln Asp Gly Ala Gly Asp Val Ala Phe Val Lys Glu Thr Thr Val Phe
    50                  55                  60

Glu Asn Leu Pro Glu Lys Ala Asp Arg Asp Gln Tyr Glu Leu Leu Cys
65                  70                  75                  80

Leu Asn Asn Ser Arg Ala Pro Val Asp Ala Phe Lys Glu Cys His Leu
            85                  90                  95

Ala Gln Val Pro Ser His Ala Val Val Ala Arg Ser Val Asp Gly Lys
```

```
                    100                 105                 110
Glu Asp Leu Ile Trp Lys Leu Leu Ser Lys Ala Gln Glu Lys Phe Gly
            115                 120                 125

Lys Asn Lys Ser Arg Ser Phe Gln Leu Phe Gly Ser Pro Pro Gly Gln
        130                 135                 140

Arg Asp Leu Leu Phe Lys Asp Ser Ala Leu Gly Phe Leu Arg Ile Pro
145                 150                 155                 160

Ser Lys Val Asp Ser Ala Leu Tyr Leu Gly Ser Arg
                165                 170

<210> SEQ ID NO 2
<211> LENGTH: 172
<212> TYPE: PRT
<213> ORGANISM: Homo sapiens

<400> SEQUENCE: 2

Phe Phe Ser Ala Ser Cys Val Pro Gly Ala Asp Lys Gly Gln Phe Pro
1               5                   10                  15

Asn Leu Cys Arg Leu Cys Ala Gly Thr Gly Glu Asn Lys Cys Ala Phe
                20                  25                  30

Ser Ser Gln Glu Pro Tyr Phe Ser Tyr Ser Gly Ala Phe Lys Cys Leu
            35                  40                  45

Arg Asp Gly Ala Gly Asp Val Ala Phe Ile Arg Glu Ser Thr Val Phe
        50                  55                  60

Glu Asp Leu Ser Asp Glu Ala Glu Arg Asp Glu Tyr Glu Leu Leu Cys
65                  70                  75                  80

Pro Asp Asn Thr Arg Lys Pro Val Asp Lys Phe Lys Asp Cys His Leu
                85                  90                  95

Ala Arg Val Pro Ser His Ala Val Val Ala Arg Ser Val Asn Gly Lys
                100                 105                 110

Glu Asp Ala Ile Trp Asn Leu Leu Arg Gln Ala Gln Glu Lys Phe Gly
            115                 120                 125

Lys Asp Lys Ser Pro Lys Phe Gln Leu Phe Gly Ser Pro Ser Gly Gln
        130                 135                 140

Lys Asp Leu Leu Phe Lys Asp Ser Ala Ile Gly Phe Ser Arg Val Pro
145                 150                 155                 160

Pro Arg Ile Asp Ser Gly Leu Tyr Leu Gly Ser Gly
                165                 170

<210> SEQ ID NO 3
<211> LENGTH: 163
<212> TYPE: PRT
<213> ORGANISM: Bos taurus

<400> SEQUENCE: 3

Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
                20                  25                  30

Ser Ile Thr Cys Val Arg Arg Ala Phe Ala Leu Glu Cys Ile Arg Ala
            35                  40                  45

Ile Ala Glu Lys Lys Ala Asp Ala Val Thr Leu Asp Gly Gly Met Val
        50                  55                  60

Phe Glu Ala Gly Arg Asp Pro Tyr Lys Leu Arg Pro Val Ala Ala Glu
65                  70                  75                  80

Ile Tyr Gly Thr Lys Glu Ser Pro Gln Thr His Tyr Tyr Ala Val Ala
```

-continued

```
                 85                  90                  95
Val Val Lys Lys Gly Ser Asn Phe Gln Leu Asp Gln Leu Gln Gly Arg
            100                 105                 110

Lys Ser Cys His Thr Gly Leu Gly Arg Ser Ala Gly Trp Val Ile Pro
            115                 120                 125

Met Gly Ile Leu Arg Pro Tyr Leu Ser Trp Thr Glu Ser Leu Glu Pro
        130                 135                 140

Leu Gln Gly Ala Val Ala Lys Phe Phe Ser Ala Ser Cys Val Pro Cys
145                 150                 155                 160

Ile Asp Arg

<210> SEQ ID NO 4
<211> LENGTH: 165
<212> TYPE: PRT
<213> ORGANISM: Homo sapiens

<400> SEQUENCE: 4

Ala Gly Arg Arg Arg Ser Val Gln Trp Cys Ala Val Ser Gln Pro
1               5                  10                  15

Glu Ala Thr Lys Cys Phe Gln Trp Gln Arg Asn Met Arg Lys Val Arg
            20                  25                  30

Gly Pro Pro Val Ser Cys Ile Lys Arg Asp Ser Pro Ile Gln Cys Ile
        35                  40                  45

Gln Ala Ile Ala Glu Asn Arg Ala Asp Ala Val Thr Leu Asp Gly Gly
    50                  55                  60

Phe Ile Tyr Glu Ala Gly Leu Ala Pro Tyr Lys Leu Arg Pro Val Ala
65                  70                  75                  80

Ala Glu Val Tyr Gly Thr Glu Arg Gln Pro Arg Thr His Tyr Tyr Ala
                85                  90                  95

Val Ala Val Val Lys Lys Gly Gly Ser Phe Gln Leu Asn Glu Leu Gln
            100                 105                 110

Gly Leu Lys Ser Cys His Thr Gly Leu Arg Arg Thr Ala Gly Trp Asn
            115                 120                 125

Val Pro Ile Gly Thr Leu Arg Pro Phe Leu Asn Trp Thr Gly Pro Pro
        130                 135                 140

Glu Pro Ile Glu Ala Ala Val Ala Arg Phe Phe Ser Ala Ser Cys Val
145                 150                 155                 160

Pro Gly Ala Asp Lys
                165

<210> SEQ ID NO 5
<211> LENGTH: 708
<212> TYPE: PRT
<213> ORGANISM: Bos taurus

<400> SEQUENCE: 5

Met Lys Leu Phe Val Pro Ala Leu Leu Ser Leu Gly Ala Leu Gly Leu
1               5                  10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80
```

```
Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
            115                 120                 125

Gln Gly Arg Lys Ser Cys His Thr Gly Leu Gly Arg Ser Ala Gly Trp
130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
            195                 200                 205

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
            275                 280                 285

Leu Leu Ser Lys Ala Gln Glu Lys Phe Gly Lys Asn Lys Ser Arg Ser
290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
            355                 360                 365

Val Gly Pro Glu Glu Gln Lys Lys Cys Gln Gln Trp Ser Gln Gln Ser
370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Thr Ser Lys Tyr Ser Ser Leu Asp Cys Val Leu Arg Pro
            435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495
```

```
Thr Gly Ser Cys Ala Phe Asp Glu Phe Ser Gln Ser Cys Ala Pro
            500                 505                 510
Gly Arg Asp Pro Lys Ser Arg Leu Cys Ala Leu Cys Ala Gly Asp Asp
        515                 520                 525
Gln Gly Leu Asp Lys Cys Val Pro Asn Ser Lys Glu Lys Tyr Tyr Gly
    530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
            580                 585                 590
Leu Asp Gly Thr Arg Lys Pro Val Thr Glu Ala Gln Ser Cys His Leu
        595                 600                 605
Ala Val Ala Pro Asn His Ala Val Val Ser Arg Ser Asp Arg Ala Ala
    610                 615                 620
His Val Lys Gln Val Leu Leu His Gln Gln Ala Leu Phe Gly Lys Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
            660                 665                 670
Arg Pro Thr Tyr Glu Glu Tyr Leu Gly Thr Glu Tyr Val Thr Ala Ile
        675                 680                 685
Ala Asn Leu Lys Lys Cys Ser Thr Ser Pro Leu Leu Glu Ala Cys Ala
    690                 695                 700
Phe Leu Thr Arg
705

<210> SEQ ID NO 6
<211> LENGTH: 711
<212> TYPE: PRT
<213> ORGANISM: Homo sapiens

<400> SEQUENCE: 6

Met Lys Leu Val Phe Leu Val Leu Leu Phe Leu Gly Ala Leu Gly Leu
1               5                   10                  15
Cys Leu Ala Gly Arg Arg Arg Ser Val Gln Trp Cys Ala Val Ser
            20                  25                  30
Gln Pro Glu Ala Thr Lys Cys Phe Gln Trp Gln Arg Asn Met Arg Lys
        35                  40                  45
Val Arg Gly Pro Pro Val Ser Cys Ile Lys Arg Asp Ser Pro Ile Gln
    50                  55                  60
Cys Ile Gln Ala Ile Ala Glu Asn Arg Ala Asp Ala Val Thr Leu Asp
65                  70                  75                  80
Gly Gly Phe Ile Tyr Glu Ala Gly Leu Ala Pro Tyr Lys Leu Arg Pro
                85                  90                  95
Val Ala Ala Glu Val Tyr Gly Thr Glu Arg Gln Pro Arg Thr His Tyr
            100                 105                 110
Tyr Ala Val Ala Val Val Lys Lys Gly Gly Ser Phe Gln Leu Asn Glu
        115                 120                 125
Leu Gln Gly Leu Lys Ser Cys His Thr Gly Leu Arg Arg Thr Ala Gly
    130                 135                 140
Trp Asn Val Pro Ile Gly Thr Leu Arg Pro Phe Leu Asn Trp Thr Gly
145                 150                 155                 160
```

```
Pro Pro Glu Pro Ile Glu Ala Ala Val Ala Arg Phe Phe Ser Ala Ser
            165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
            210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
            245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
            275                 280                 285

Asn Leu Leu Arg Gln Ala Gln Glu Lys Phe Gly Lys Asp Lys Ser Pro
            290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
            325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
            370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Glu
            405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
            485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
            515                 520                 525

Gly Asp Glu Gln Gly Glu Asn Lys Cys Val Pro Asn Ser Asn Glu Arg
            530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
            565                 570                 575
```

```
Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
                660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
        690                 695                 700

Ala Cys Glu Phe Leu Arg Lys
705                 710

<210> SEQ ID NO 7
<211> LENGTH: 35
<212> TYPE: PRT
<213> ORGANISM: Artificial Sequence
<220> FEATURE:
<223> OTHER INFORMATION: synthetic peptide

<400> SEQUENCE: 7

Glu Pro Tyr Phe Gly Tyr Ser Gly Ala Phe Lys Cys Leu Gln Asp Gly
1               5                   10                  15

Ala Gly Asp Val Ala Phe Val Lys Glu Thr Thr Val Phe Glu Asn Leu
            20                  25                  30

Pro Glu Lys
        35

<210> SEQ ID NO 8
<211> LENGTH: 11
<212> TYPE: PRT
<213> ORGANISM: Artificial Sequence
<220> FEATURE:
<223> OTHER INFORMATION: synthetic peptide

<400> SEQUENCE: 8

Ser Val Asp Gly Lys Glu Asp Leu Ile Trp Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetic peptide

<400> SEQUENCE: 9

Val Asp Ser Ala Leu Tyr Leu Gly Ser Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic peptide
```

```
<400> SEQUENCE: 10

Phe Phe Ser Ala Ser Cys Val Pro Cys Ile Asp Arg
1               5                   10

<210> SEQ ID NO 11
<211> LENGTH: 26
<212> TYPE: PRT
<213> ORGANISM: Artificial Sequence
<220> FEATURE:
<223> OTHER INFORMATION: synthetic peptide

<400> SEQUENCE: 11

Trp Phe Lys Cys Arg Arg Trp Gln Trp Arg Met Lys Lys Leu Gly Ala
1               5                   10                  15

Pro Ser Ile Thr Cys Val Arg Arg Ala Phe
            20                  25

<210> SEQ ID NO 12
<211> LENGTH: 11
<212> TYPE: PRT
<213> ORGANISM: Artificial Sequence
<220> FEATURE:
<223> OTHER INFORMATION: synthetic peptide

<400> SEQUENCE: 12

Trp Cys Thr Ile Ser Gln Pro Glu Trp Phe Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: synthetic peptide

<400> SEQUENCE: 13

Lys Leu Gly Ala Pro Ser Ile Thr Cys Val Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic peptide

<400> SEQUENCE: 14

Arg Ala Phe Ala Leu Glu Cys Ile Arg
1               5

<210> SEQ ID NO 15
<211> LENGTH: 21
<212> TYPE: PRT
<213> ORGANISM: Artificial Sequence
<220> FEATURE:
<223> OTHER INFORMATION: synthetic peptide

<400> SEQUENCE: 15

Lys Ala Asp Ala Val Thr Leu Asp Gly Gly Met Val Phe Glu Ala Gly
1               5                   10                  15

Arg Asp Pro Tyr Lys
            20

<210> SEQ ID NO 16
```

```
<211> LENGTH: 12
<212> TYPE: PRT
<213> ORGANISM: Artificial Sequence
<220> FEATURE:
<223> OTHER INFORMATION: synthetic peptide

<400> SEQUENCE: 16

Leu Arg Pro Val Ala Ala Glu Ile Tyr Gly Thr Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic peptide

<400> SEQUENCE: 17

Glu Ser Pro Gln Thr His Tyr Tyr Ala Val Ala Val Val Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: synthetic peptide

<400> SEQUENCE: 18

Lys Gly Ser Asn Phe Gln Leu Asp Gln Leu Gln Gly Arg
1               5                   10

<210> SEQ ID NO 19
<211> LENGTH: 65
<212> TYPE: PRT
<213> ORGANISM: Artificial Sequence
<220> FEATURE:
<223> OTHER INFORMATION: synthetic peptide

<400> SEQUENCE: 19

Leu Gln Gly Ala Val Ala Lys Phe Phe Ser Ala Ser Cys Val Pro Cys
1               5                   10                  15

Ile Asp Arg Gln Ala Tyr Pro Asn Leu Cys Gln Leu Cys Lys Gly Glu
            20                  25                  30

Gly Glu Asn Gln Cys Ala Cys Ser Ser Arg Glu Pro Tyr Phe Gly Tyr
        35                  40                  45

Ser Gly Ala Phe Lys Cys Leu Gln Asp Gly Ala Gly Asp Val Ala Phe
    50                  55                  60

Val
65
```

LACTOFERRIN FRAGMENTS AND USE THEREOF

FIELD OF THE INVENTION

The present invention is directed to novel lactoferrin fragments and uses thereof. The invention provides diagnostic compositions and methods for detecting inflammatory resolution and for distinguishing resolving and non-resolving inflammatory reactions.

BACKGROUND OF THE INVENTION

Inflammation is a biological response to injury, infection or irritation in which a cascade of cellular and microvascular reactions serves to eradicate the infection, remove damaged tissue and generate new tissue. During this process, elevated permeability in microvessels allows neutrophils and mononuclear cells to leave the intravascular compartment, and perform various anti-microbial activities to eradicate the injury. The final stage of inflammation is resolution, a process characterized by active blockade of leukocyte infiltration, followed by their apoptosis and the removal of cellular and molecular debris from inflamed sites, enabling tissue to return to homeostasis.

Many inflammatory diseases fail to resolve, resulting in an excessive and potentially harmful inflammatory response. Such excessive responses are implicated in a number of common diseases such as cancer, asthma, atherosclerosis, autoimmune diseases, Alzheimer's and Parkinson's disease, among others.

A hallmark of the resolution phase is the removal of apoptotic cells, mediated by phagocytes such as macrophages and dendritic cells. In contrast to the clearance of pathogens by phagocytosis which commonly triggers an immune response, the engulfment of apoptotic cells is generally considered anti-inflammatory.

Resolution is considered a biosynthetically active process and a number of key factors and chemical mediators have been found to influence its development, including lipoxins, resolvins, protectins, maresins, eicosanoids, polyunsaturated fatty acids (PUFAs), glucocorticoids, annexin and ω-3 fatty acids, among others. Many of these mediators promote resolution by stimulating macrophage uptake of apoptotic neutrophils and preventing necrosis-driven secondary inflammation.

Some of the molecular features underlying the resolution of acute inflammation have been disclosed by some of the inventors of the present invention (Bannenberg et al. J. Immunol. 2005, 1; 174(7):4345-55) and include specific anti-inflammatory mediators such as lipoxin, resolvins, protectins and intermediates in their generation as molecular pathways of resolution.

A new population of macrophages, typically referred to as $CD11b^{low}$ macrophages, has recently been identified by some of the inventors of the present invention (Schif-Zuck et al. Eur J. Immunol. 2011 41(2):366-79). These macrophages display pro-resolving properties during the resolution of an acute inflammatory response such as increased engulfment of apoptotic leukocytes compared to other classes of macrophages, among other features.

Among the various factors found to take part in inflammatory processes is the 80 kDa glycoprotein lactoferrin. Lactoferrin belongs to the transferrin protein family, characterized by the ability to bind and transfer $Fe^{3+}$ ions. Three different isoforms of lactoferrin have been isolated: lactoferrin-α, capable of iron binding but having no ribonuclease activity, and lactoferrin-β and γ, which possess ribonuclease activity, but are not capable of binding iron. Lactoferrin comprises a single polypeptide chain of about 700 amino acids in length folded into two globular lobes, the C- (carboxy) and N- (amino) terminal regions.

The primary cells involved in lactoferrin synthesis are myeloid cells and secretory epithelia. The highest levels of lactoferrin are found in colostrums, milk and seminal plasma; lactoferrin is also found in most mucosal secretions such as uterine fluid, vaginal secretion, saliva, bile, pancreatic juice, small intestine secretions, nasal secretion, and tears. In addition, lactoferrin is found in specific granules of neutrophils, which, following degranulation, are believed to be the main source of lactoferrin in blood plasma. It has been shown that lactoferrin concentration in the plasma increases during most inflammatory reactions and some viral infections (Kanyshkova et al. Biochemistry 2001, 66(1):1-7.).

Lactoferrin represents one of the first defense systems against pathogens, exhibiting antimicrobial, antibacterial, antiviral and antiparasitic activity. Lactoferrin was also found to influence immune system cells both positively and negatively. On one hand, it has been reported to support proliferation, differentiation, and activation of immune cells and strengthen the immune response. On the other hand, lactoferrin has also been reported to have anti-inflammatory properties, in reducing the production of some pro-inflammatory cytokines such as tumor necrosis factor alpha (TNF-α), interleukin 1 beta (IL-1β) and interleukin 6 (IL-6), among others. In addition, lactoferrin has been reported to mediate inhibition of tumor growth and to possess several other biologic activities, including a ribonuclease activity (capable of RNA hydrolysis) and an osteogenic activity.

With the exception of iron binding, the biological activities of lactoferrin are thought to reside in a highly basic domain in the N-terminal region, designated lactoferricin. This part of the protein is released in the stomach at acidic pH by pepsin. Bovine lactoferricin is a highly potent 25aa peptide corresponding to residues 17-41 of lactoferrin, whereas the fragment released from human lactoferrin is larger (including positions 1-41) and has weaker antimicrobial properties. A number of lactoferricin derivatives have been described and tested, which retain at least a part of the activities of the native domain. An antimicrobial peptide derived from ovotransferrin, called OTAP-92, has also been identified, corresponding to positions 109-200 of ovotransferrin (Vogel et al., Biochem Cell Biol. 2002; 80(1):49-63).

Japanese Patent Application Publication No. JP 2004155751 discloses a peptide capable of suppressing the production of inflammatory cytokines such as TNF-α and IL-6, wherein the peptide used may be bovine lactoferrin hydrolyzed with a protease.

U.S. Patent Application Publication No. 2007/0197426 discloses polypeptide fragments of lactoferrin comprising the amino acid sequence of phenylalanine, lysine and aspartic acid, obtained by degradation with serine proteases such as elastase, wherein the molecular weight of said fragments is preferably less than 25 kDa. Specifically, disclosed are fragments of human lactoferrin of 21-25 kDa, with N-termini located at positions 240, 288 and 341. These fragments are described as having pro-inflammatory effects, such as inducing cytokine and chemokine production. The disclosed lactoferrin fragments are said to be distinct from pro-inflammatory lactoferrin fragments having a molecular weight of 30 to 60 kDa previously identified in bovine mastitis, reported by Japanese Patent Application Publication No. JP2003/289749. US '426 further discloses the production of four short synthetic peptides corresponding to positions 243-249, 251-259, 287-293 and 295-307 of human lactoferrin, wherein two of these peptides, namely those corresponding to positions 243-249 and 295-307, demonstrated an inflammation-promoting activity.

Komine et al. (Mol. Immunol. 2007 March; 44(7):1498-508) refers to certain lactoferrin fragments identified in parotid saliva of human periodontitis patients, with N-termini located at positions 4, 238, 286 and 340 for the 32, 23, 22 and 19 kDa fragments, respectively, characterized by low Con A affinity. The amounts of these fragments in saliva were reported to increase in periodontitis in association with the severity of the clinical symptoms. It is further indicated that a longitudal study is required to verify whether the elevated levels of these fragments subsequently decrease to the levels of healthy control subjects or whether persons who have high levels of these fragments may possess a predisposition to periodontal disease.

Komine et al. (J Vet Med. Sci. 2006 July; 68(7):715-23) identified fragments of 38, 23, 22 and 14 kDa, generated from elastase-treated bovine lactoferrin. The publication discloses that the amino acid sequences of the 22 and 23 kDa fragments correspond to positions 237-416 and 285-449 of bovine lactoferrin, respectively. These fragments were shown to have a pro-inflammatory activity, promoting cytotoxicity and leukocyte infiltration, through induction of pro-inflammatory cytokines and chemokines (TNF-α, IL-6, IL-8 and MCP-1), and suggested to take part in the initiation or progression of inflammation. The publication further discloses that measurements of the bovine lactoferrin concentration is used in Japan as a clinical marker for bovine mastitis in lactating cows.

Certain lactoferrin fragments having low Con A affinity and have also been described by Komine et al. (J Vet Med. Sci. 2006 March; 68(3):205-11; J Vet Med. Sci. 2005 July; 67(7):667-77) in healthy or mastitic mammary gland secretions. The N-terminal positions are 237, 285 and 240 for the 23, 22 and 19 kDa fragments, respectively. It is disclosed that the concentrations of these fragments increased in mastitis in correlation to the severity of the symptoms, and decreased after antibiotic therapy. In addition, considerable fluctuations in the concentration of the low Con A affinity fragments have been detected over time in drying cows.

Nowhere in the background art is it taught or disclosed that lactoferrin or fragments thereof may be used as molecular markers for defining the resolution phase of inflammation. There remains an unmet need for identification of molecular signals that differentiate between resolving and non-resolving inflammation, thereby facilitating a more suitable and effective treatment to inflammatory diseases.

SUMMARY OF THE INVENTION

The present invention for the first time provides protein markers that appear when an inflammatory process enters a phase of resolution. The invention provides methods for diagnosing the inflammation state of a subject with an inflammatory ailment. Thus, the present invention provides methods for assessing whether a subject with an inflammation has entered the resolution phase. According to additional embodiments, the invention identifies for the first time lactoferrin fragments enabling the distinction of subjects with inflammation in resolution from non-resolving inflamed subjects and healthy individuals.

The present invention is based in part on the unexpected discovery that murine macrophages that have engulfed apoptotic neutrophils, degrade lactoferrin and secrete the fragments generated. It was further discovered that lactoferrin fragments of different sizes are generated during different stages of inflammation associated with E. coli mammary infection. Surprisingly, a novel lactoferrin fragment, having a molecular weight of about 17 kDa as determined by SDS-polyacrylamide gel electrophoresis (SDS-PAGE), was identified in milk of spontaneously resolving cows following E. coli infection, whereas in milk from cows that did not clear the infection (i.e. did not enter the resolution phase), no such lactoferrin fragment was identified.

Kinetic analyses revealed that the levels of two other lactoferrin fragments (of 23 and 15 kDa) decreased over time until infection and inflammation were resolved, whereas the amount of the 17 kDa fragment increased over time in resolving cows. In contrast, in non-resolving cows, appearance of the 23 kDa fragment was very late compared to resolving cows and the levels of the smaller fragments were very low, whereas in milk obtained from healthy cows, lactoferrin and its fragments were barely detectable. The amount of the 17 kDa fragment, as well as the relative quantities of lactoferrin fragments, advantageously expressed as the ratio between the amounts of the 23 and 17 kDa fragments in a sample, have thus been unexpectedly identified as diagnostic markers for transition from inflammation to resolution.

These findings were further validated in an in vivo murine peritonitis model, in which Lactoferrin fragments were surprisingly found to be released to the interstitial space in spleen and inguinal lymph nodes. Six distinguishable fragments of 50, 37, 23, 21, 17 and 15 kDa (as evaluated by SDS-PAGE), were detectable in addition to the full length 78 kDa protein. The 17 kDa fragment was unexpectedly identified as a common marker for resolving inflammation, as the amount of this fragment consistently increased during resolution in both splenic and lymph node fluids.

Thus, according to embodiments of the invention, the presence or amounts of isolated lactoferrin fragments obtained from inflammatory tissues or secretory fluids of a subject reflects whether the subject has begun clinical recovery or not. The methods of the invention may hence be used for determining whether to apply a treatment to a subject, thereby saving unnecessary, expensive and potentially harmful treatments from subjects who have already entered the recovery track.

According to certain embodiments, provided are methods for assessing the presence or absence of inflammation in resolution in a subject, comprising determining the molecular weight of at least one lactoferrin fragment in a sample obtained from the subject.

According to a first aspect of the present invention, there is provided a method for assessing resolution of inflammation in a subject, comprising determining the presence or amount of a lactoferrin fragment characteristic of resolution in a sample obtained from the subject. According to embodiments of the invention, the fragment is characterized by a molecular weight of about 17 kDa.

According to some embodiments, the fragment characteristic of resolution, useful as a diagnostic marker in the methods of the invention, comprises an amino acid sequence corresponding to positions 172-342 of mammalian lactoferrin, for example bovine lactoferrin (e.g. positions 172-342 of SEQ ID NO: 5) or human lactoferrin (e.g. positions 172-342 of SEQ ID NO: 6).

According to one embodiment, the method comprises determining the presence of the lactoferrin fragment, wherein the presence of the fragment in said sample indicates that said subject has inflammation in resolution.

According to another embodiment, the molecular weight of said fragment is 17 kDa (e.g. as evaluated by SDS-PAGE).

According to yet another embodiment, the method further comprises quantifying the amount of the lactoferrin fragment in the sample, wherein the presence of said fragment in said sample, in an amount significantly higher that its amount in a control sample corresponding to a subject having active (non-resolving) inflammation and/or a healthy subject, indicates that said subject has inflammation in resolution.

According to yet another embodiment, the method further comprises quantifying the amounts of the lactoferrin fragments in said sample, and determining the ratio of the amount of the lactoferrin fragment characteristic of resolution (having a molecular weight of about 17 kDa) to the amount of a lactoferrin fragment having a molecular weight of about 23 kDa. According to yet another embodiment, a ratio significantly higher than determined for a control sample corresponding to a subject having non-resolving inflammation indicates that said subject has inflammation in resolution. According to yet another embodiment, a ratio of at least 2 indicates that said subject has inflammation in resolution.

According to yet another embodiment, the method further comprises quantifying the amounts of the lactoferrin fragments in said sample, and determining the ratio of the amount of the lactoferrin fragment characteristic of resolution (having a molecular weight of about 17 kDa) to the amount of a lactoferrin fragment having a molecular weight of about 15 kDa. In another embodiment said fragments comprise an amino acid sequence corresponding to positions 172-342 and 20-182 of mammalian lactoferrin, for the about 17 kDa and about 15 kDa fragments, respectively. According to yet another embodiment, a ratio significantly higher than determined for a control sample corresponding to a subject having non-resolving inflammation indicates that said subject has inflammation in resolution. According to yet another embodiment, a ratio of at least 2 indicates that said subject has inflammation in resolution. According to yet another embodiment, a ratio of at least 3 indicates that said subject has inflammation in resolution.

According to another aspect, the present invention provides a method for monitoring the progression of inflammatory resolution in a subject in need thereof, comprising determining the amount of the lactoferrin fragment characteristic of resolution having a molecular weight of about 17 kDa in a first sample obtained from the subject at a first time point, and in a second sample obtained from said subject at a second subsequent time point. In another embodiment, an increase in the amount of said fragment in the second sample compared to the first sample indicates a positive progression of inflammatory resolution. According to another embodiment, the method further comprises determining the amount of a lactoferrin fragment having a molecular weight of about 23 kDa in said first and second samples and determining the ratio of the amount of said fragment of about 17 kDa to the amount of said fragment of about 23 kDa in each sample, wherein an increase in the ratio in said second sample compared to said first sample indicates a positive progression in inflammatory resolution.

In another aspect there is provided a method for determining whether a subject having an inflammatory disease is a candidate for a treatment for the disease, comprising assessing the resolution of inflammation in the subject by determining the presence of a lactoferrin fragment characteristic of resolution, having a molecular weight of about 17 kDa, in a sample obtained from said subject, wherein the absence of resolution indicates that said subject is a candidate for the treatment.

According to one embodiment, assessing the resolution of inflammation is performed by determining the level of the lactoferrin fragment of about 17 kDa, wherein the presence of said fragment in said sample indicates that said subject has inflammation in resolution.

According to another embodiment, assessing the resolution of inflammation is performed by a method comprising quantifying the amounts of the lactoferrin fragments in said sample, and determining the ratio of the amount of a lactoferrin fragment having a molecular weight of about 17 kDa to the amount of a lactoferrin fragment having a molecular weight of about 23 kDa, wherein a ratio significantly higher than that determined for a control sample corresponding to a subject having non-resolving inflammation indicates that said subject has inflammation in resolution. In another embodiment, a ratio of at least 2 indicates that said subject has inflammation in resolution.

According to yet another embodiment, the treatment comprises an antibacterial drug, an antiviral drug, an antifungal drug or an anti-parasitic drug.

In the methods of the invention, according to some embodiments, the subject is suspected of having an inflammatory disease. According to yet another embodiment the subject is diagnosed with an inflammatory disease.

According to yet another embodiment of the methods of the invention, the subject is selected from humans and non-human mammals. In another embodiment the subject is human. In another embodiment the subject is selected from livestock and domestic animals. According to yet another embodiment the subject is livestock. According to yet another embodiment the subject is a dairy animal (e.g. bovine or ovine). According to yet another embodiment the subject is a lactating mammal. According to yet another embodiment the subject is bovine.

According to yet another embodiment of the methods of the invention the inflammatory disease is an autoimmune disease. In another embodiment the inflammatory disease is associated with an infection, e.g. a bacterial infection, viral infection, fungal infection or parasitic infection. According to a particular embodiment the inflammatory disease is associated with *E. coli* infection. In another embodiment the inflammatory disease is mastitis (e.g. *E. coli* induced mastitis). In another embodiment the inflammatory disease is peritonitis.

According to other embodiments of the methods of the invention the sample is obtained from an inflammatory tissue or from body fluids of the subject. According certain embodiments the samples may be obtained from e.g. milk, blood, urine and lymph samples, or from other mucosal secretions (e.g. uterine fluid, vaginal secretion, saliva, bile, pancreatic juice, small intestine secretions, nasal secretion, colostrums and tears), wherein each possibility represents a separate embodiment of the invention. In some embodiments, the sample is obtained in a noninvasive manner (e.g. milk samples, urine samples or saliva samples). In some embodiments, the sample is separated (e.g. by centrifugation) to a cell-enriched fraction (cellular fraction) and a substantially cell-free fraction (soluble fraction). In another embodiment, the molecular weight of the lactoferrin fragments (or their presence or amount) is determined in the cellular fraction of the sample. In another embodiment the molecular weight of the lactoferrin fragments (or their presence or amount) is determined in the soluble fraction of the sample. In a particular embodiment, the subject is a lactating mammal (e.g. a lactating cattle) and the sample is a milk sample.

According to yet another embodiment of the methods of the invention determining the molecular weight (or the presence or amount) of lactoferrin fragments is performed by a method comprising an immunoassay (e.g. molecular weight separation by gel electrophoresis and Western blot analysis using lactoferrin-specific antibodies).

According to other embodiments, the lactoferrin fragment having a molecular weight of about 17 kDa, identified as a fragment characteristic of resolution useful as a diagnostic marker in the methods of the invention, comprises at least one (and preferably 2, 3 or 4) of SEQ ID NOs: 7-10. According to another embodiment, said fragment comprises SEQ ID NOs: 7-10. In certain other embodiments, said fragment is further characterized in that it does not contain at least one (and preferably 2-8) of SEQ ID NOs: 11-18. In another embodiment said fragment is further characterized in that it does not contain SEQ ID NOs: 11-18.

In a particular embodiment the lactoferrin is bovine lactoferrin and said fragment has an amino acid sequence as set forth in SEQ ID NO: 1.

In another particular embodiment the lactoferrin is human lactoferrin and said fragment has an amino acid sequence as set forth in SEQ ID NO: 2.

In other embodiments, the lactoferrin fragment having a molecular weight of about 15 kDa described herein comprises at least one (and preferably 2-8) of SEQ ID NOs: 10-18. According to another embodiment, said fragment comprises SEQ ID NOs: 11-18. In certain other embodiments, said fragment is further characterized in that it does not contain at least one (and preferably 2-4) of SEQ ID NOs: 7-9. In another embodiment said fragment does not contain SEQ ID NOs: 7-9.

In another embodiment the lactoferrin fragment having a molecular weight of about 15 kDa described herein has an amino acid sequence corresponding to positions 20-182 of mammalian lactoferrin (e.g. bovine or human). For example, the sequence may comprise any one of SEQ ID NOs: 3 and 4.

In another aspect, the invention provides an isolated lactoferrin fragment characteristic of resolution having a molecular weight of about 17 kDa, the fragment having an amino acid sequence as set forth in any one of SEQ ID NOs: 1 and 2 or at least 90% amino acid identity thereto. In a particular embodiment, the fragment is selected from the group consisting of SEQ ID NOs: 1 and 2.

In another aspect, there is provided an isolated lactoferrin fragment having a molecular weight of about 15 kDa, the fragment having an amino acid sequence as set forth in any one of SEQ ID NOs: 3 and 4 or at least 90% amino acid identity thereto. In a particular embodiment, the fragment is selected from the group consisting of SEQ ID NOs: 3 and 4.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2A shows lactoferrin fragments obtained from cellular and soluble milk fractions in resolving cows at the indicated time points after infection. FIG. 2B shows lactoferrin fragments obtained from cellular and soluble milk fractions in non-resolving cows at the indicated time points after infection and of lactoferrin fragments obtained from healthy cows ("Healthy").

DETAILED DESCRIPTION OF THE INVENTION

Figure 1:
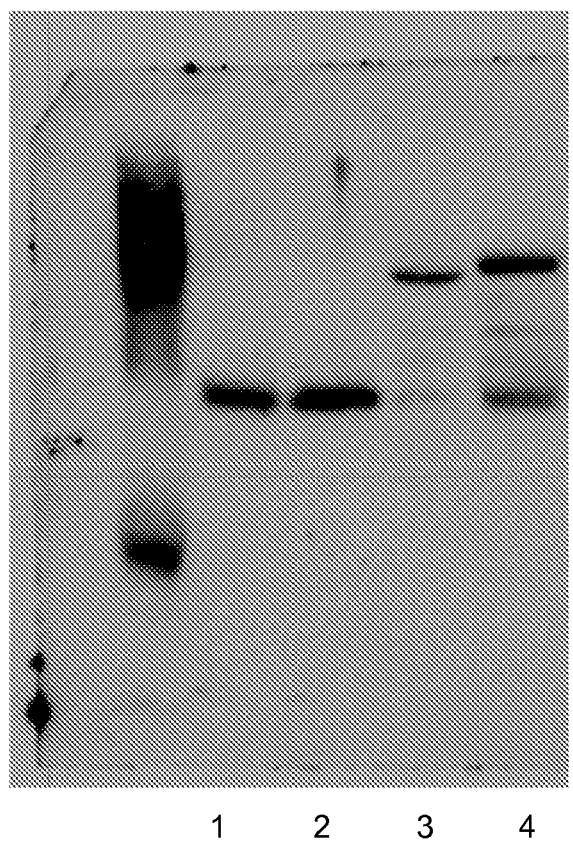
FIG. 1 Shows lactoferrin fragments obtained from macrophages (lane 1), macrophages incubated with apoptotic Jurkat cells (lane 2), apoptotic neutrophils (lane 3) and macrophages incubated with apoptotic neutrophils (lane 4).

The present invention is directed to novel lactoferrin fragments and uses thereof. The present invention provides diagnostic compositions and methods for assessing the presence or absence of resolving inflammation and for monitoring the progression of inflammatory resolution in a subject. Also disclosed are methods for treating a subject having an inflammatory disease, comprising determining whether the subject has resolving inflammation by determining the molecular weight of lactoferrin fragments.

"Resolution of inflammation", "inflammatory resolution" and "resolution" are used herein interchangeably and refer to an active process controlled by endogenous 'pro-resolving' mediators, which terminates an inflammatory reaction and leads to the restoration of the inflamed tissue to its prior physiological function. According to some embodiments, endogenous mediators controlling this process may limit leukocyte trafficking to the inflamed site, reverse vasodilation and vascular permeability, and/or promote the removal of inflammatory leukocytes, exudate and fibrin. The terms "inflammation in resolution" and "resolving inflammation" as used herein indicate the clinical state of a subject with inflammation undergoing resolution. Typically, resolving inflammation indicates an inflammatory state in which at least 50% of the leukocytes infiltrating the inflammatory site are macrophages. In some embodiments, resolving inflammation corresponds to the period between maximal infiltration of polymorphonuclear cells (PMN) to the inflamed site and complete remission of inflammation. Thus, subjects with inflammation in resolution are distinguished from healthy subjects in which complete remission has been accomplished, as well as from subjects in which the inflammatory process is increasing or is in steady state. In other embodiments, in a subject with inflammation in resolution the pathogen or inducer of inflammation has been cleared from the inflammatory site; however, some inflammatory processes may still progress in the absence of the inducing pathogen.

As used herein, "positive progression of resolution" means enhancement or augmentation of the resolution process as described herein, leading to reduction or subsequent termination of the inflammatory process. Positive progression of resolution is typically associated with a positive outcome of the inflammatory disease or condition.

According to a first aspect of the present invention, there is provided a method for assessing the presence or absence of resolving inflammation in a subject. In some embodiments, the methods comprise determining the molecular weights of lactoferrin fragments in a sample obtained from the subject. According to alternate or additional embodiments, the methods comprise determining the presence or amount of a lactoferrin fragment characteristic of resolution in said sample, as described herein.

According to some embodiments, the method further comprises comparing the molecular weights of the lactoferrin fragments in the sample to those of fragments in control samples corresponding to (e.g. obtained from) subjects having resolving inflammation, non-resolving inflammation and/or healthy subjects.

In some embodiments, the method further comprises determining the presence of a lactoferrin fragment characteristic of resolution in said sample. In one embodiment, the fragment is characterized by a molecular weight comparable to that of a lactoferrin fragment obtained from subjects having resolving inflammation but not to that of a lactoferrin fragment obtained from subjects having non-resolving inflammation. In another embodiment, the lactoferrin fragment characteristic of resolution has a molecular weight comparable to that of a lactoferrin fragment obtained from subjects having resolving inflammation but not to that of a lactoferrin fragment obtained from subjects having non-resolving inflammation or healthy subjects. According to these embodiments, the presence of a lactoferrin fragment characteristic of resolution in said sample indicates that said subject has resolving inflammation.

In another embodiment, the molecular weight of the lactoferrin fragment characteristic of resolution is higher than 15 kDa. In another embodiment, the molecular weight of said fragment is lower than 23 kDa. In various embodiments, the molecular weight of said fragment is between 16-22, 16-20, 16-19, 16-18 or 17-18 kDa. In particular embodiments, the molecular weight of said fragment is about 17 kDa, 18 kDa or 19 kDa.

The term "about" as used herein means approximately, roughly or around of, typically extending the boundaries 10% above and below the numerical values set forth. Thus, for example, "about 17 kDa" means 16-19 kDa and "about 23 kDa" means 21-24 kDa.

In a further particular embodiment, the molecular weight of said fragment is essentially 17 kDa. The term essentially as used herein with reference to a molecular weight typically means up to 0.5 kDa above or below the molecular weight set forth. In a further particular embodiment, the molecular weight of said fragment is essentially 18 kDa. In a further particular embodiment, the molecular weight of said fragment is essentially 19 kDa. In an additional particular embodiment, the molecular weight of said fragment is 17 kDa. In a further particular embodiment, the molecular weight of said fragment is 18 kDa. In a further particular embodiment, the molecular weight of said fragment is 19 kDa. Each possibility represents a separate embodiment of the invention.

According to certain other embodiments, the lactoferrin fragment characteristic of resolution is produced by macrophages following incubation with apoptotic neutrophils (e.g. following ex vivo incubation for 24 hrs at a macrophage:neutrophil ratio of at least 1:5). According to some particular embodiments, said fragment is produced by $CD11b^{low}$ macrophages, characterized by surface expression of CD11b which is about 5-10 times lower than its mean surface expression on inflammatory peritoneal macrophages.

According to other embodiments, the method further comprises quantifying the amount of said fragment in said sample. In another embodiment, the presence of a lactoferrin fragment characteristic of resolution in said sample, in an amount significantly higher than its amount in a control sample corresponding to a subject having non-resolving inflammation and/or a healthy subject, indicates that said subject has resolving inflammation.

In various embodiments, a "control sample corresponding to a subject" may refer to a sample obtained from a subject, a combined sample obtained from a pool of subjects, or a pre-stored reference value (e.g. in a sample obtained from a subject, or the mean value in a combined sample obtained from a pool of subjects).

According to other embodiments, the method further comprises quantifying the amounts of two or more lactoferrin fragments having different molecular weights in said sample and determining the amount ratio of the fragments. According to additional embodiments, the method further comprises comparing said ratio to that of fragments in control samples corresponding to subjects having resolving inflammation, non-resolving inflammation and/or healthy subjects.

According to various embodiments, the method may further comprise quantifying the amount of a fragment of about (or essentially) 15, 23, 25, 30 and/or 50 kDa, wherein each possibility represents a separate embodiment of the invention. In a particular embodiment, the method comprises quantifying the amounts of fragments of about 17 kDa and about 23 kDa.

According to another embodiment, the ratio between the amount of lactoferrin fragments having a molecular weight of about 17 kDa to that of lactoferrin fragments having a molecular weight of about 23 kDa is determined. In some embodiments, a ratio significantly higher than that determined for control sample corresponding to a subject having non-resolving inflammation indicates that said subject has resolving inflammation. In certain particular embodiments, a ratio of at least about 2 indicates that said subject has resolving inflammation. In other particular embodiments, a ratio of at least 2 indicates that said subject has inflammation in resolution. In yet further particular embodiments, a ratio of 2, 3, 4, 5, 6 or more indicates that said subject has inflammation in resolution, wherein each possibility represents a separate embodiment of the invention.

In alternate or additional embodiments, the ratio between the amount of lactoferrin fragments having a molecular weight of about 17 kDa to that of lactoferrin fragments having a molecular weight of about 15 kDa is determined. In some embodiments, a ratio significantly higher than that determined for control sample corresponding to a subject having non-resolving inflammation indicates that said subject has resolving inflammation. In certain particular embodiments, a ratio of at least about 2, 10, 50, 100 or 200 indicates that said subject has inflammation in resolution.

In another embodiment there is provided a method for assessing the presence or absence of resolving inflammation in a subject, comprising determining the presence of a lactoferrin fragment having a molecular weight of about 17 kDa, wherein the presence of the fragment in said sample indicates that said subject has resolving inflammation.

In another embodiment there is provided a method for assessing the presence or absence of resolving inflammation in a subject, comprising determining the amount of a lactoferrin fragment having a molecular weight of about 17 kDa, wherein the presence of the fragment in said sample in an amount significantly higher than its amount in a control sample corresponding to a subject having non-resolving inflammation indicates that said subject has resolving inflammation.

In yet another embodiment, the methods of the invention are suitable for monitoring the progression of inflammation in a subject in need thereof. According to some embodiments, an increase over time in the amount of the about 17 kDa fragment, or in other embodiments in the ratio of the amount of lactoferrin fragments having a molecular weight of about 17 kDa to that of lactoferrin fragments having a molecular weight of about 23 kDa, indicates an increase or positive progression of the resolution process.

According to a further embodiment the methods of the invention are suitable for determining whether a subject is amenable for treatment for an inflammatory disease, wherein if a subject is diagnosed as having resolving inflammation according to the methods of the invention, then said subject is not amenable for the treatment.

According to another aspect, the present invention provides a method for treating a subject having an inflammatory disease, comprising a) determining the molecular weights of lactoferrin fragments in a sample obtained from the subject, b) determining whether the subject has resolving inflammation as described herein, and c) if said subject does not have resolving inflammation, providing said subject with treatment for the disease. For example, according to specific embodiments, step b) may be performed by determining the level of a lactoferrin fragment of 16-22 kDa, preferably about 17 kDa, or the ratio between the amount of lactoferrin fragments having a molecular weight of about 17 kDa to that of lactoferrin fragments having a molecular weight of about 23 kDa, as detailed herein.

Subjects, Diseases and Samples

In the methods of the invention, according to some embodiments, the subject is suspected of having an inflammatory disease. According to other embodiments the subject is diagnosed with an inflammatory disease.

According to yet another embodiment the subject is selected from humans and non-human mammals. In another embodiment the subject is human. In another embodiment the subject is selected from livestock and domestic animals. According to yet another embodiment the subject is livestock. According to yet another embodiment the subject is a dairy animal (e.g. bovine or ovine). According to yet another embodiment the subject is a lactating mammal. According to yet another embodiment the subject is bovine.

The term "livestock animals" as used herein refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus Ovis, domestic goats and other members of the genus Capra; domesticated quadrupeds being raised for specialized tasks such as use as a beast of burden, e.g., an equine animal including domestic horses and other members of the family Equidae, genus Equus, or for searching and sentinel duty.

The term "domestic animals" includes mammals such as e.g., a canine animal including domestic dogs and other members of the genus Canis; and domesticated quadrupeds being raised primarily for recreational purposes, e.g., members of Equus and Canis, as well as a feline animal including domestic cats and other members of the family Felidae, genus Felis.

According to yet another embodiment the inflammatory disease is an autoimmune disease (e.g. systemic lupus erythematosus (SLE), rheumatoid arthritis (RA), inflammatory bowel disease (Crohn's disease, ulcerative colitis) and autoimmune hepatitis). In another embodiment the inflammatory disease is associated with an infection. For example, the inflammatory disease may be associated with a bacterial infection, viral infection (e.g. influenza, West Nile virus) fungal infection or parasitic infection. According to a particular embodiment the inflammatory disease is associated with E. coli infection. In another embodiment the inflammatory disease is mastitis (e.g. E. coli induced mastitis). In another embodiment the disease is peritonitis. In other embodiments, the disease may be associated with various other primary or secondary infections, e.g. chronic obstructive pulmonary disease (COPD), chronic granulomatous disease (CGD) or hepatitis.

As used herein the term "mastitis" refers to an inflammation of a mammary gland or an udder. Mastitis is most commonly caused by bacterial invasion and their toxins. It has been described in humans, cows, sheep, goats, pigs, horses, and rabbits. Mastitis causes lactating women to experience pain when nursing the child, it damages mammary tissue, and the formation of scar tissue in the breast may cause disfigurement. In dairy cattle, mastitis is believed to be the most economically important disease.

In subclinical mastitis, no swelling of the breast or udder is detected nor are there observable abnormalities in the milk. Special screening tests, however, such as the California Mastitis Test (CMT), Wisconsin Mastitis Test (WMT) based on an estimation of somatic cell counts and the catalase test will show changes in the milk composition. This type of mastitis is commonly referred to as "hidden".

Clinical mastitis can be mild or acute, and is characterized by the presence of leukocytes in the milk. Mild clinical mastitis involves changes in the milk appearance including presence of flakes or clots, watery milk or other unusual forms of the milk. Mild clinical mastitis may be accompanied by other symptoms including hot, sensitive or swollen breast or udder.

Severe clinical mastitis involves the symptoms of hot, sensitive, firm breast or udder that is quite painful to the lactating animal. The onset of severe clinical mastitis is sudden and the lactating animal may become ill showing signs of fever, rapid pulse, depression, weakness and loss of appetite. When the whole lactation system of the animal is affected, the condition is referred to as acute systemic mastitis. The severe symptoms may be also accompanied with cessation of milk production.

Chronic mastitis is persistent udder infection, typically in the form of subclinical mastitis, which occasionally can develop into the clinical form and back to the subclinical form. Chronic mastitis is characterized by hard lump within the mammary gland due to the establishment of bacteria and the formation of connective tissue.

Mastitis can be caused by bacteria; for example, bovine mastitis may be caused primarily by bacteria and/or may be caused by yeasts and molds. In some cases the causes of bovine mastitis are unknown and could be due to physical trauma or weather extremes. Although bovine mastitis can be caused by many different bacterial species, the most common are the *Staphylococcus* and *Streptococcus* species. The most common staphylococci and streptococci causing bovine mastitis include *Staphylococcus aureus, Streptococcus dysgalactiae, Streptococcus equinus, Streptococcus agalactiae, Staphylococcus hyicus, Staphylococcus simulans, Staphylococcus epidermidis, Staphylococcus chromogenes* and *Staphylococcus xylosus*. Other staphylococci and streptococci known to cause bovine mastitis include *Staphylcoccus oxford, Staphylococcus aureus* WCUH29, *Streptococcus pneumoniae* ERY2, *Streptococcus pneumoniae* 1629, *Streptococcus pneumoniae* N 1387, *Enterococcus faecalis* I, *Enterococcus faecalis* 7, *Haemophilus influenzae* QI, *Haemophilus influenzae* NEMC1, *Moraxella catarrhalis* 1502, *Escherichia coli* 7623 AcrABEFD+, *Escherichia coli* 120 AcrAB−, *Escherichia coli* MG1655, or *Escherichia coli* MG1658. In some embodiments, the organism may be methicillin-resistant *Staphylococcus aureus*.

In some embodiments, bovine mastitis may also be caused by gram-negative bacteria, or by organisms such as *Pseudomonas aeruginosa, Brucella melitensis, Corynebacterium bovis*, various species of *Mycoplasma, Escherichia coli, Klebsiella pneumoniae, Klebsiella oxytoca, Enterobacter aerogenes*, various species of *Pasteurella, Arcanobacterium pyogenes*, various species of *Proteus, Prototheca zopfii* (e.g., achlorophyllic algae), and *Prototheca wickerhamii* (e.g., achlorophyllic algae).

Examples 2 and 4 herein demonstrate detection of a fragment of about 17 kDa as assessed by SDS-PAGE, in milk samples obtained from cows resolving from clinical mastitis induced by or associated with infection of *E. coli* (Example 2) or various pathogens (Example 4).

Treatment of the affected animal includes antibiotics (e.g. by intramammary injections) to eliminate the respective bacteria, and anti-inflammatory agents to reduce swelling.

For example, intramammary dry cow therapy reduces the number of contagious infections during the dry period and environmental streptococcal infections during the early dry period. The dry cow preparations are formulated (vehicles, solvents, pH) to cause minimal tissue irritation, to avoid damaging the secretory tissue and to prevent fibrosis. An antibiotic which is active against Gram-positive organisms in low concentrations is chosen, and if combinations are used, antibiotics with bactericidal effects are preferable. Antibiotic combinations of cloxacillin, ampicillin, cephapirin, streptomycin, cephalexin, penethamate, erythromycin, amoxicillin, penicillin, nafcillin are frequently used, according to acceptable protocols.

Antibiotic treatment of subclinical mastitis during lactation is cost effective and increases the opportunities for drug residues in milk. According to the Food and Drug Administration/Center for Veterinary Medicine the approved antibiotics for the treatment of bovine mastitis are: pirlimycin, methicillin, cloxacillin, amoxicillin, novobiocin, penicillin G, dihydrostreptomycin, cephapirin and erythromycin. The choice of the antimicrobial agents and the route of administration is directed by the characteristics of the drug and regulatory issues. Many antimicrobial drugs used for mastitis treatment, including compounds that penetrate the mammary gland, are sulfonamides, penicillins with the exception of penethamate iodide, aminoglycosides, and early-generation cephalosporins.

Peritonitis is inflammation of the peritoneal cavity. The most serious cause is perforation of the GI tract, which causes immediate chemical inflammation followed shortly by infection from intestinal organisms. Peritonitis can also result from any abdominal condition that causes marked inflammation (e.g., appendicitis, diverticulitis, strangulating intestinal obstruction, pancreatitis, pelvic inflammatory disease, mesenteric ischemia). Intraperitoneal blood from any source (e.g., ruptured aneurysm, trauma, surgery, ectopic pregnancy) is irritating and results in peritonitis. Peritoneosystemic shunts, drains, and dialysis catheters in the peritoneal cavity predispose a patient to infectious peritonitis, as does ascitic fluid. Spontaneous bacterial peritonitis may occur, in which the peritoneal cavity is infected by blood-borne bacteria.

Peritonitis causes fluid shift into the peritoneal cavity and bowel, leading to severe dehydration and electrolyte disturbances. Adult respiratory distress syndrome can develop rapidly, with following kidney failure, liver failure, and disseminated intravascular coagulation.

Infectious peritonitis can be classified as primary, secondary, or tertiary. In primary peritonitis (also called spontaneous bacterial peritonitis), the source of infection does not arise from the gastrointestinal tract, and there is no identifiable anatomical derangement of the intra-abdominal viscera. Primary peritonitis is mostly caused by a chronic liver disease, such as cirrhosis. In contrast, secondary peritonitis is due to an infection of the abdominal viscera, and may arise as a consequence of perforation, ischemic necrosis, or penetrating injury. Tertiary peritonitis is defined as peritonitis that persists or recurs after more than one failed source control procedure, and is highly frequent in patients requiring intensive care unit admission for severe abdominal infections. The most common organisms implicated in bacterial peritonitis are *Escherichia coli, Pseudomonas aeruginosa, Staphylococcus aureus, C. perfingens, Neisseria gonorrhea, Chlamydia trachomatis, Mycobaterium tuberculosis, Chlamydia trachomatis, Clostridium perfringens*, streptococci and enteroococci. The most common fungal agents to cause infectious peritonitis are *Candida albicans, Candida parapsilasis*, and *Aspergillus fumigaus*. Such infections are treated by the respective antibiotics or other anti-bacterial or anti-fungal agent, as known in the art.

For instance Example 3 demonstrates detection of a 17 kDa lactoferrin fragment in spleen and lymph node interstitial fluids during resolution in a mouse peritonitis model. Example 1 demonstrates that murine macrophages characteristic of resolving peritonitis are capable of acquiring lactoferrin from apoptotic PMN and degrading it to smaller fragments, wherein Example 3 demonstrates that a 17 kDa lactoferrin fragment is eventually released at the spleen and lymph node.

According to yet another embodiment the sample is obtained from an inflammatory tissue or from body fluids of the subject. According to certain embodiments the lactoferrin fragments may be obtained from fluid samples, including but not limited to milk (or mammary secretions), blood, urine and lymph samples, and samples obtained from other mucosal secretions (e.g. uterine fluid, vaginal secretion, saliva, bile, pancreatic juice, small intestine secretions, nasal secretion, colostrums and tears), wherein each possibility represents a separate embodiment of the invention. In some embodiments, the sample is obtained in a noninvasive manner (e.g. milk samples, urine samples saliva samples). In some embodiments, the sample is separated (e.g. by centrifugation) to a cell-enriched fraction (cellular fraction) and a substantially cell-free fraction (soluble fraction). In another embodiment, the molecular weight of the lactoferrin fragments (or their presence or amount) is determined in the cellular fraction of the sample. In another embodiment the molecular weight of the lactoferrin fragments (or their presence or amount) is determined in the soluble fraction of the sample. In a particular embodiment, the subject is a lactating mammal (e.g. a lactating cattle) and the sample is a milk sample. Tissue or fluid samples to be used in the methods of the invention may be obtained and optionally further purified, diluted or otherwise processed using methods well known in the art. Non-limitative examples for obtaining, purifying and processing various biological samples are presented in the Examples section herein.

Diagnostic Methods and Means

According to yet another embodiment determining the molecular weight of lactoferrin (and/or detecting the presence or amount of specific lactoferrin fragments) is performed by an immunoassay. By means of a non-limiting example, the methods of the invention may involve molecular weight separation by gel electrophoresis and Western blot analysis using lactoferrin-specific antibodies. In other embodiments, various other immunoassays may be utilized, e.g. Enzyme-linked immunosorbent assay (ELISA) using antibodies directed to specific lactoferrin fragments (capable of specifically binding and differentiating between different fragments) or assays based on dipstick technology or antibody array. In some embodiments, the methods of the invention are suitable for automated or semi-automated analysis, and may enable clinical, medium or high-throughput screening of multiple samples. For example, automated ELISA systems such as Biotest's Quickstep® ELISA Processor, Maxmat Automated microwell ELISA analyzer (Maxmat S. A., France), or DSX™ Four-Plate System (Dynex Technologies) may conveniently be used. Such techniques are well known to the ordinarily skilled artisan and have been described in many standard immunology manuals and texts.

For instance, Examples 1-4 herein demonstrate detection of lactoferrin fragments and evaluation of their molecular weight gel separation using sodium dodecyl sulfate polyacrylamide gel electrophoresis (SDS-PAGE) 7-10%, transfer to a nitrocellulose membrane and blotting using an anti-lactoferrin polyclonal IgG (sc-25622, Santa Cruz Biotechnology) and labeled secondary antibody. As demonstrated in these examples, the lactoferrin fragment characteristic of resolution was determined by this method to be of about 17 kDa. Although the presence of detergents such as SDS act to denature the polypeptides and equalize their charges such that their migration rate should be proportional to their size and independent of other factors such as shape and charge, it is noted, that certain polypeptides may still be influenced by these additional factors during SDS-PAGE separation. Thus, for example, a polypeptide evaluated as having a molecular weight of 17 kDa using SDS-PAGE separation may be up to 10% longer or shorter as determined by sequence analysis.

In some embodiments, without limitation, evaluating the molecular weight of lactoferrin fragments according to the invention by gel electrophoresis may be performed in 7-10% SDS-PAGE in the presence of 1-3% SDS, at 80-120V e.g. 80V for 30 minutes for upper gel and 120V for 90 minutes for lower gel. Samples may be boiled e.g. for 5 min in sample buffer which may contain in one exemplary embodiment (for sample buffer ×2) 150 mM Tris pH 6.8, 20% glycerol, 4% SDS, 5% β-mercaptoethanol, and 15 ug/ml bromophenol blue. Variations and modifications to the exemplary embodiments and parameters may be made by the skilled artisan to adjust the assay as required.

In another aspect, there is provided a kit for assessing the presence or absence of resolving inflammation in a subject, comprising means for determining the molecular weights of lactoferrin fragments and/or determining the presence or amount of a lactoferrin fragment characteristic of resolution, as described herein.

For example, the kit may comprise one or more lactoferrin-specific antibodies and/or reference samples comprising one or more lactoferrin fragments (e.g. the fragments having an amino acid sequence as set forth in SEQ ID NOs: 1-4).

In one embodiment there is provided a kit for assessing the presence or absence of resolving inflammation in a subject, comprising means for determining the presence of a lactoferrin fragment characteristic of resolution having a molecular weight of about 17 kDa in a sample. According to particular embodiments, the lactoferrin fragment characteristic of resolution comprises a sequence corresponding to positions 172-342 of mammalian lactoferrin, e.g. SEQ ID NOs: 1 or 2.

In another embodiment, the means comprise an antibody specifically recognizing an isolated lactoferrin fragment characteristic of resolution having a molecular weight of about 17 kDa, the fragment having an amino acid sequence as set forth in any one of SEQ ID NOs: 1 and 2.

In another embodiment, the kit further comprises one or more isolated lactoferrin fragments, selected from:
  an isolated fragment characteristic of resolution having a molecular weight of about 17 kDa, the fragment having an amino acid sequence as set forth in any one of SEQ ID NOs: 1 and 2 or at least 90% amino acid identity thereto, and
  an isolated lactoferrin fragment having a molecular weight of about 15 kDa, the fragment having an amino acid sequence as set forth in any one of SEQ ID NOs: 3 and 4 or at least 90% amino acid identity thereto.

In another embodiment, the kit further comprises instructions for diagnosing resolving inflammation, wherein the presence of said fragment in said sample, e.g. in an amount significantly higher than its amount in a control sample corresponding to a subject having non-resolving inflammation and/or a healthy subject, indicates that said subject has inflammation in resolution.

In another aspect, there is provided an antibody specifically recognizing an isolated lactoferrin fragment characteristic of resolution having a molecular weight of about 17 kDa, the fragment having an amino acid sequence as set forth in any one of SEQ ID NOS: 1 and 2.

The terms "antibody" or "antibodies" as used herein refer to an antibody or fragments thereof, including, but not limited to, a full length antibody having a human immunoglobulin constant region, a monoclonal IgG, a single chain antibody, a humanized monoclonal antibody, an F(ab')$_2$ fragment, an F(ab) fragment, an Fv fragment, a labeled antibody, an immobilized antibody and an antibody conjugated with a heterologous compound. Each possibility represents a separate embodiment of the invention. In one embodiment, the antibody is a monoclonal antibody. In another embodiment, the antibody is a polyclonal antibody. In another embodiment, the antibody is a humanized antibody.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Besides the conventional method of raising antibodies in vivo, antibodies can be generated in vitro using phage display technology, by methods well known in the art (e.g. Current Protocols in Immunology, Colligan et al (Eds.), John Wiley & Sons, Inc. (1992-2000), Chapter 17, Section 17.1).

An antigen (e.g. a lactoferrin fragment of the invention) or immunogenic complex (e.g. an epitope specific to said fragment conjugated to a protein carrier such as BSA) can be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art. The antisera obtained can be used directly (e.g. as diluted sera or as purified polyclonal antibodies), or monoclonal antibodies may be obtained, as described herein.

A monoclonal antibody (mAb) is a substantially homogeneous population of antibodies to a specific antigen. mAbs may be obtained by methods known to those skilled in the art. See, for example U.S. Pat. No. 4,376,110; Ausubel et al ("Current Protocols in Molecular Biology," Volumes I-III, John Wiley & Sons, Baltimore, Md., 1994). A hybridoma producing a mAb may be cultivated in vitro or in vivo. High titers of mAbs can be obtained in in vivo production where cells from the individual hybridomas are injected intraperitoneally into pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Antibody fragments may be obtained using methods well known in the art. (See, for example, Harlow, E. and Lane, D. (1988). Antibodies: A Laboratory Manual, Cold Spring Harbor Laboratory, New York). For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, F(ab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

An Fv is composed of paired heavy chain variable and light chain variable domains. This association may be non-covalent. Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art. Improved bivalent miniantibodies, with identical avidity as whole antibodies, may be produced by high cell density fermentation of Escherichia coli. (U.S. Pat. No. 4,946,778).

After antibodies have been obtained, they may be tested for activity, for example via enzyme-linked immunosorbent assay (ELISA).

In various embodiments, the antibodies of the present invention specifically bind to a lactoferrin fragment (e.g. a fragment of about 17 kDa characteristic of resolution as described herein). The terms "specific binding" or "specifically binds" refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the association constant $K_A$ is higher than $10^6$ $M^{-1}$. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques. The term "specifically recognizing" further indicate that the binding of an antibody to an antigen is not competitively inhibited by the presence of non-related molecules (e.g. other lactoferrin fragments as described herein). Conveniently, detection of the capacity of an antibody to specifically bind an antigen, e.g. a lactoferrin fragment, may be performed by quantifying specific antigen-antibody complex formation (e.g. by ELISA).

Identifying an appropriate epitope useful for raising antibodies specific to the fragment characteristic of resolution is within the abilities of those skilled in the art. As the respective amino acid positions of this fragment and other lactoferrin fragments are set forth herein or are known in the art, one of skill in the art would be able to choose a region within the fragment of about 17 kDa which does not overlap with the fragment of about 15 kDa, or other fragments identified in the art.

In another aspect the invention provides a method for assessing resolution of inflammation in a subject, comprising determining the presence of a lactoferrin fragment characteristic of resolution having a molecular weight of about 17 kDa in a sample obtained from the subject.

In one embodiment, said fragment comprises an amino acid sequence corresponding to positions 172-342 of mammalian lactoferrin.

In another embodiment, the method comprises quantifying the amount of the lactoferrin fragment in the sample, wherein the presence of said fragment in said sample, in an amount significantly higher than its amount in a control sample corresponding to a subject having non-resolving inflammation and/or a healthy subject, indicates that said subject has inflammation in resolution.

In another embodiment, the method further comprises quantifying the amounts of lactoferrin fragments in said sample, and determining the ratio of the amount of the lactoferrin fragment characteristic of resolution to the amount of a lactoferrin fragment having a molecular weight of about 23 kDa, wherein a ratio significantly higher than that determined for a control sample corresponding to a subject having non-resolving inflammation indicates that said subject has inflammation in resolution. In a particular embodiment, a ratio of at least 2 indicates that said subject has inflammation in resolution.

In another embodiment, the method further comprises quantifying the amounts of lactoferrin fragments in said sample, and determining the ratio of the amount of the lactoferrin fragment characteristic of resolution to the amount of a lactoferrin fragment having a molecular weight of about 15 kDa, wherein said fragments comprise an amino acid sequence corresponding to positions 172-342 and 20-182 of mammalian lactoferrin, respectively, and wherein a ratio significantly higher than that determined for a control sample corresponding to a subject having non-resolving inflammation indicates that said subject has inflammation in resolution. In a particular embodiment, a ratio of at least 3 indicates that said subject has inflammation in resolution.

In another embodiment, the fragment characteristic of resolution having a molecular weight of about 17 kDa comprises SEQ ID NOs: 7-10.

In another embodiment the lactoferrin is bovine lactoferrin. In a particular embodiment said fragment has an amino acid sequence as set forth in SEQ ID NO: 1.

In another embodiment the lactoferrin is human lactoferrin. In a particular embodiment said fragment has an amino acid sequence as set forth in SEQ ID NO: 2.

In another embodiment the subject is selected from humans and non-human mammals. In a particular embodiment the subject is human. In another particular embodiment the subject is bovine. In another embodiment the subject is a lactating mammal.

In another embodiment the inflammation is associated with an infection. According to various embodiments, the infection is a bacterial infection, a viral infection, a fungal infection or a parasitic infection. In a particular embodiment the inflammatory disease is associated with *E. coli* infection. In another particular embodiment said inflammatory disease is mastitis. In yet another particular embodiment the inflammatory disease is peritonitis.

In another embodiment the sample is obtained from an inflammatory tissue or from body fluids of the subject. According to various embodiments, the sample is obtained from body fluids selected from the group consisting of milk, blood, urine and lymph samples, and samples obtained from uterine fluid, vaginal secretion, saliva, bile, pancreatic juice, small intestine secretions, nasal secretion, colostrums and tears. In a particular embodiment the sample is a milk sample.

In another embodiment the method is used for monitoring the progression of inflammatory resolution in a subject in need thereof, the method further comprising determining the amount of the lactoferrin fragment characteristic of resolution having a molecular weight of about 17 kDa in a first sample obtained from the subject at a first time point, and in a second sample obtained from said subject at a second subsequent time point. In another embodiment an increase in the amount of said fragment in the second sample compared to the first sample indicates a positive progression of inflammatory resolution. In another embodiment the method further comprises determining the amount of a lactoferrin fragment having a molecular weight of about 23 kDa in said first and second samples and determining the ratio of the amount of said fragment of about 17 kDa to the amount of said fragment of about 23 kDa in each sample, wherein an increase in the ratio in said second sample compared to said first sample indicates a positive progression in inflammatory resolution.

In another aspect there is provided a method for determining whether a subject having an inflammatory disease is a candidate for a treatment for the disease, comprising assessing the resolution of inflammation in the subject by determining the presence of a lactoferrin fragment characteristic of resolution having a molecular weight of about 17 kDa in a sample obtained from said subject, wherein the absence of resolution indicates that said subject is a candidate for the treatment.

In one embodiment the presence of the fragment in said sample indicates that said subject has inflammation in resolution. In another embodiment, the method comprises quantifying the amounts of the lactoferrin fragments in said sample, and determining the ratio of the amount of a lactoferrin fragment having a molecular weight of about 17 kDa to the amount of a lactoferrin fragment having a molecular weight of about 23 kDa, wherein a ratio significantly higher than that determined for a control sample corresponding to a subject having non-resolving inflammation indicates that said subject has inflammation in resolution.

In another embodiment said fragment comprises an amino acid sequence corresponding to positions 172-342 of mammalian lactoferrin. In a particular embodiment said fragment has an amino acid sequence as set forth in any one of SEQ ID NOs: 1 and 2.

In another aspect there is provided an isolated lactoferrin fragment characteristic of resolution having a molecular weight of about 17 kDa, the fragment having an amino acid sequence as set forth in any one of SEQ ID NOs: 1 and 2 or at least 90% amino acid identity thereto. In some embodiments the fragment is selected from the group consisting of SEQ ID NOs: 1 and 2.

In another aspect there is provided an isolated lactoferrin fragment having a molecular weight of about 15 kDa, the fragment having an amino acid sequence as set forth in any one of SEQ ID NOs: 3 and 4 or at least 90% amino acid identity thereto. In some embodiments the fragment is selected from the group consisting of SEQ ID NOs: 3 and 4.

In another aspect the invention provides an antibody specifically recognizing an isolated lactoferrin fragment characteristic of resolution having a molecular weight of about 17 kDa, the fragment having an amino acid sequence as set forth in any one of SEQ ID NOs: 1 and 2.

In another aspect the invention provides a kit for assessing the presence or absence of resolving inflammation in a subject, comprising means for determining the presence of a lactoferrin fragment characteristic of resolution having a molecular weight of about 17 kDa in a sample.

In another embodiment, the means comprise an antibody specifically recognizing an isolated lactoferrin fragment characteristic of resolution having a molecular weight of about 17 kDa, the fragment having an amino acid sequence as set forth in any one of SEQ ID NOs: 1 and 2.

In another embodiment, the kit further comprises one or more isolated lactoferrin fragments, selected from:
- an isolated fragment characteristic of resolution having a molecular weight of about 17 kDa, the fragment having an amino acid sequence as set forth in any one of SEQ ID NOs: 1 and 2 or at least 90% amino acid identity thereto, and
- an isolated lactoferrin fragment having a molecular weight of about 15 kDa, the fragment having an amino acid sequence as set forth in any one of SEQ ID NOs: 3 and 4 or at least 90% amino acid identity thereto.

Lactoferrin Fragments

In another aspect, the invention provides a purified lactoferrin fragment of about 17 kDa, which may be isolated from a sample obtained from a subject having resolving inflammation. The fragment is characterized by a molecular weight comparable to that of a lactoferrin fragment obtained from subjects having resolving inflammation but not to that of a lactoferrin fragment obtained from subjects having non-resolving inflammation. The fragment may be isolated and purified from the sample using methods well known in the art (e.g. by gel electrophoresis, gel filtration and affinity chromatography using lactoferrin-specific antibodies). For example, the fragment may be isolated from milk samples or lymph samples, as demonstrated herein. Alternatively, the fragment may be produced by recombinant or synthetic methods known in the art.

Thus, the invention relates in some embodiments to an isolated lactoferrin fragment characteristic of resolution having a molecular weight of about 17 kDa. The term "isolated" as used herein with respect to lactoferrin fragments is meant to denote a polypeptide in a substantially pure form corresponding to a naturally occurring lactoferrin fragment which may be found in a mammalian cell, tissue or bodily fluid, and which may be hence isolated from such natural sources, or prepared synthetically or by recombinant methods, and is obtained in isolated form irrespective of the actual way by which said polypeptide is produced. The term "substantially pure" means that the polypeptide is substantially (typically at least 80% or 90%) devoid of other polypeptides, e.g. of other lactoferrin fragments.

The amino acid sequence of bovine lactoferrin may be represented by SEQ ID NO: 5, accession no. AAA30610, as follows:

```
                                              (SEQ ID NO: 5)
MKLFVPALLS LGALGLCLAA PRKNVRWCTI SQPEWFKCRR

WQWRMKKLGA PSITCVRRAF ALECIRAIAE KKADAVTLDG

GMVFEAGRDP YKLRPVAAEI YGTKESPQTH YYAVAVVKKG

SNFQLDQLQG RKSCHTGLGR SAGWVIPMGI LRPYLSWTES

LEPLQGAVAK FFSASCVPCI DRQAYPNLCQ LCKGEGENQC

ACSSREPYFG YSGAFKCLQD GAGDVAFVKE TTVFENLPEK

ADRDQYELLC LNNSRAPVDA FKECHLAQVP SHAVVARSVD

GKEDLIWKLL SKAQEKFGKN KSRSFQLFGS PPGQRDLLFK

DSALGFLRIP SKVDSALYLG SRYLTTLKNL RETAEEVKAR

YTRVVWCAVG PEEQKKCQQW SQQSGQNVTC ATASTTDDCI

VLVLKGEADA LNLDGGYIYT AGKCGLVPVL AENRKTSKYS
```

```
SLDCVLRPTE GYLAVAVVKK ANEGLTWNSL KDKKSCHTAV

DRTAGWNIPM GLIVNQTGSC AFDEFFSQSC APGRDPKSRL

CALCAGDDQG LDKCVPNSKE KYYGYTGAFR CLAEDVGDVA

FVKNDTVWEN TNGESTADWA KNLNREDFRL LCLDGTRKPV

TEAQSCHLAV APNHAVVSRS DRAAHVKQVL LHQQALFGKN

GKNCPDKFCL FKSETKNLLF NDNTECLAKL GGRPTYEEYL

GTEYVTAIAN LKKCSTSPLL EACAFLTR.
```

The amino acid sequence of human lactoferrin may be represented by SEQ ID NO: 6, accession no. AAA59511, as follows:

```
                                              (SEQ ID NO: 6)
MKLVFLVLLF LGALGLCLAG RRRRSVQWCA VSQPEATKCF

QWQRNMRKVR GPPVSCIKRD SPIQCIQAIA ENRADAVTLD

GGFIYEAGLA PYKLRPVAAE VYGTERQPRT HYYAVAVVKK

GGSFQLNELQ GLKSCHTGLR RTAGWNVPIG TLRPFLNWTG

PPEPIEAAVA RFFSASCVPG ADKGQFPNLC RLCAGTGENK

CAFSSQEPYF SYSGAFKCLR DGAGDVAFIR ESTVFEDLSD

EAERDEYELL CPDNTRKPVD KFKDCHLARV PSHAVVARSV

NGKEDAIWNL LRQAQEKFGK DKSPKFQLFG SPSGQKDLLF

KDSAIGFSRV PPRIDSGLYL GSGYFTAIQN LRKSEEEVAA

RRARVVWCAV GEQELRKCNQ WSGLSEGSVT CSSASTTEDC

IALVLKGEAD AMSLDEGYVY TAGKCGLVPV LAENYKSQQS

SDPDPNCVDR PVEGYLAVAV VRRSDTSLTW NSVKGKKSCH

TAVDRTAGWN IPMGLLFNQT GSCKFDEYFS QSCAPGSDPR

SNLCALCIGD EQGENKCVPN SNERYYGYTG AFRCLAENAG

DVAFVKDVTV LQNTDGNNNE AWAKDLKLAD FALLCLDGKR

KPVTEARSCH LAMAPNHAVV SRMDKVERLK QVLLHQQAKF

GRNGSDCPDK FCLFQSETKN LLFNDNTECL ARLHGKTTYE

KYLGPQYVAG ITNLKKCSTS PLLEACEFLR K.
```

According to some embodiments, the fragment characteristic of resolution useful as a diagnostic marker in the methods of the invention comprises an amino acid sequence corresponding to positions 172-342 of mammalian lactoferrin, for example bovine lactoferrin (e.g. positions 172-342 of SEQ ID NO: 5) or human lactoferrin (e.g. positions 172-342 of SEQ ID NO: 6). In another embodiment the fragment comprises an amino acid sequence corresponding to positions 171-343 of mammalian lactoferrin.

According to some embodiments, the fragment having a molecular weight of about 17 kDa useful as a diagnostic marker in the methods of the invention comprises at least one (and preferably 2, 3 or 4) of the following sequences: EPYFGYSGAFKCLQDGAGDVAFVKETTVFENLPEK, SVDGKEDLIWK, VDSALYLGSR and FFSASCVPCIDR (SEQ ID NOs: 7-10, respectively). According to another embodiment, said fragment comprises SEQ ID NOs: 7-10. It is noted that SEQ ID NOs: 7-10 correspond to positions 206-240, 278-288, 333-342 and 171-182 of bovine lactoferrin, respectively. In another embodiment, the fragment comprises one or more homologs of SEQ ID NOs: 7-10 from other mammalian lactoferrins (e.g. having the corresponding amino acid positions as set forth above). In certain other embodiments, said fragment is further characterized in that it does not contain at least one (and preferably 2-8) of the following sequences: WFKCRRWQWRMKKLGAPSITCVRRAF, WCTISQPEWFK, KLGAPSITCVR, RAFALECIR, KADAVTLDGGMVFEAGRDPYK, LRPVAAEIYGTK, ESPQTHYYAVAWK and KGSNFQLDQLQGR (SEQ ID NOs: 11-18, respectively). In another embodiment said fragment does not contain SEQ ID NOs: 11-18. In another embodiment, said fragment is recognized by an antibody directed against an epitope within the sequence LQGAVAKFFSASCVPCIDRQAYPNLCQLCKGEGENQCACSSREPYFGYSG AFKCLQDGAGDVAFV (SEQ ID NO: 19), e.g. sc-25622 (rabbit anti-mouse lactoferrin polyclonal sera, Santa Cruz Biotechnology, Inc.).

According to some embodiments, the fragment having a molecular weight of about 17 kDa useful as a diagnostic marker in the methods of the invention comprises an amino acid sequence corresponding to positions 172-342 of mammalian lactoferrin (e.g. bovine lactoferrin or human lactoferrin). In a particular embodiments, the fragment corresponds to positions 171-342 of bovine lactoferrin (e.g. of SEQ ID NO: 5). In another particular embodiments, the fragment corresponds to positions 172-343 of human lactoferrin (e.g. of SEQ ID NO: 6). Each possibility represents a separate embodiment of the invention.

In another particular embodiment the lactoferrin is bovine lactoferrin and said fragment has an amino acid sequence as set forth in SEQ ID NO: 1, as follows:

```
                                          (SEQ ID NO: 1)
FFSASCVPCIDRQAYPNLCQLCKGEGENQCACSSREPYFGYSGAFK

CLQDGAGDVAFVKETTVFENLPEKADRDQYELLCLNNSRAPVDAFKE

CHLAQVPSHAVVARSVDGKEDLIWKLLSKAQEKFGKNKSRSFQLFGS

PPGQRDLLFKDSALGFLRIPSKVDSALYLGSR.
```

In another embodiment said fragment has at least 90% amino acid identity to SEQ ID NO: 1. In yet another particular embodiment, said fragment consist essentially of an amino acid sequence as set forth in SEQ ID NO: 1. In yet another particular embodiment, said fragment consist of an amino acid sequence as set forth in SEQ ID NO: 1.

In another particular embodiment the lactoferrin is human lactoferrin and said fragment has an amino acid sequence as set forth in SEQ ID NO: 2, as follows:

```
                                          (SEQ ID NO: 2)
FFSASCVPGADKGQFPNLCRLCAGTGENKCAFSSQEPYFSYSGAFK

CLRDGAGDVAFIRESTVFEDLSDEAERDEYELLCPDNTRKPVDKFKD

CHLARVPSHAVVARSVNGKEDAIWNLLRQAQEKFGKDKSPKFQLFG

SPSGQKDLLFKDSAIGFSRVPPRIDSGLYLGSG.
```

In another embodiment said fragment has at least 90% amino acid identity to SEQ ID NO: 2. In yet another particular embodiment, said fragment consist essentially of an amino acid sequence as set forth in SEQ ID NO: 2. In yet another particular embodiment, said fragment consist of an amino acid sequence as set forth in SEQ ID NO: 2.

In a particular embodiment, the fragment is selected from the group consisting of SEQ ID NOs: 1 and 2.

According to other embodiments, the invention relates to an isolated lactoferrin fragment of about 15 kDa. The fragment is herein identified in samples collected during inflammation, and is thus useful in the diagnostic methods of the invention (e.g. for determining the ratio of the fragment of about 17 kDa to about 15 kDa as detailed herein). The fragment comprises at least one (and preferably 2-9) of SEQ ID NOs: 10-18. According to another embodiment, said fragment comprises SEQ ID NOs: 10-18. It is noted that SEQ ID NOs: 10-18 correspond to positions 171-182, 35-60, 27-37, 47-57, 58-66, 72-92, 93-104, 105-118 and 119-131 of bovine lactoferrin, respectively. In another embodiment, the fragment comprises one or more homologs of SEQ ID NOs: 10-18 from other mammalian lactoferrins (e.g. having the corresponding amino acid positions as set forth above). In certain other embodiments, said fragment is further characterized in that it does not contain at least one (and preferably 2-3) of SEQ ID NOs: 7-9. In another embodiment said fragment does not contain SEQ ID NOs: 7-9.

In other embodiments, the fragment comprises an amino acid sequence corresponding to positions 20-182 of mammalian lactoferrin. In other embodiments, the fragment comprises an amino acid sequence corresponding to positions 19-183 of mammalian lactoferrin. In other embodiments, the fragment comprises an amino acid sequence corresponding to positions 27-182 of mammalian (e.g. bovine) lactoferrin. In other embodiments, the fragment comprises an amino acid sequence corresponding to positions 27-183 of mammalian (e.g. human) lactoferrin. In a particular embodiment, the fragment corresponds to positions 20-182 of bovine lactoferrin. In another particular embodiment, the fragment corresponds to positions 19-183 of human lactoferrin.

In another aspect, the isolated lactoferrin fragment having a molecular weight of about 15 kDa, has an amino acid sequence as set forth in any one of SEQ ID NOs: 3 and 4, as follows:

```
                                     (bovine, SEQ ID NO: 3)
NVRWCTISQPEWFKCRRWQWRMKKLGAPSITCVRRAFALECIRAIAE

KKADAVTLDGGMVFEAGRDPYKLRPVAAEIYGTKESPQTHYYAVAVV

KKGSNFQLDQLQGRKSCHTGLGRSAGWVIPMGILRPYLSWTESLEP

LQGAVAKFFSASCVPCIDR;
and (human, SEQ ID NO: 4)
AGRRRRSVQWCAVSQPEATKCFQWQRNMRKVRGPPVSCIKRDSPI

QCIQAIAENRADAVTLDGGFIYEAGLAPYKLRPVAAEVYGTERQPRTH

YYAVAVVKKGGSFQLNELQGLKSCHTGLRRTAGWNVPIGTLRPFLN

WTGPPEPIEAAVARFFSASCVPGADK.
```

In another embodiment said fragment has at least 90% amino acid identity to SEQ ID NOs: 3 or 4.

In a particular embodiment, the fragment is selected from the group consisting of SEQ ID NOs: 3 and 4.

Each possibility represents a separate embodiment of the invention.

Polypeptides and peptides may conveniently be produced by recombinant technology. Recombinant methods for designing, expressing and purifying proteins and peptides are known in the art (see, e.g. Sambrook et al., 1989, 1992, 2001, Molecular Cloning: A Laboratory Manual, Cold Springs Harbor Laboratory, New York). Nucleic acid molecules may include DNA, RNA, or derivatives of either DNA or RNA. An isolated nucleic acid sequence encoding a polypeptide or peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Polynucleotides that include more or less nucleotides can result in the same or equivalent proteins. Using recombinant production methods, selected host cells, e.g. of a microorganism such as $E.$ $coli$ or yeast, are transformed with a hybrid viral or plasmid DNA vector including a specific DNA sequence coding for the polypeptide or polypeptide analog and the polypeptide is synthesized in the host upon transcription and translation of the DNA sequence.

In various embodiments, the sequences may be derived directly from the corresponding sequence of the lactoferrin polypeptide or fragment (such that they may be identical to a portion of a sequence of lactoferrin) or may contain certain derivatizations and substitutions. Thus in some embodiments the use of salts and functional derivatives of these sequences are contemplated, as long as they retain the respective biologic functions and at least 90% sequence identity, as detailed herein. Accordingly the present invention encompasses polypeptide homologs containing non-natural amino acid derivatives or non-protein side chains. The homologs of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of the peptide of the invention may be used, as long as the biological activities of the peptide are maintained.

The present invention encompasses derivatives containing non-natural amino acid derivatives or non-protein side chains. The polypeptides and derivatives may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of the polypeptides and peptides utilized in methods of the invention may be used, as long as the biological activities of the polypeptide are maintained.

The amino acid residues described herein are preferred to be in the "L" isomeric form. However, residues in the "D" isomeric form can be substituted for any L-amino acid residue, as long as the peptide substantially retains the desired functional property.

Chemical derivatives may have one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a derivative can differ from the natural sequence of the polypeptides or peptides of the invention by chemical modifications including, but are not limited to, terminal-$NH_2$ acylation, acetylation, or thioglycolic acid amidation, and by terminal-carboxlyamidation, e.g., with ammonia, methylamine, and the like.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Experimental Procedures

Peritonitis Induction and Leukocyte Isolation

Neutrophils and macrophages were isolated from peritoneal exudates as follows: Male C57BL/6 mice (6-8 wk; protocol approved by the Committee of Ethics, University of Haifa) were injected I.P. with zymosan A (1 mg in 1 ml). After 24 hr (for neutrophils) or 66 hr (for macrophages) mice were euthanized with $CO_2$ and peritoneal exudates were collected by lavaging with 5 ml of sterile saline. Exudate cells were stained on ice for 20 min with PE-conjugated rat anti-mouse Ly-6G (clone RBC-8C5) or PE-conjugated rat anti-mouse F4/80 (clone CI:A3-1), and washed twice with 1% BSA in PBS. Then, neutrophils or macrophages were isolated using magnetic bead-conjugated anti-PE antibodies and a separation kit (Stem cell) according to the manufacturer's instructions. Macrophages were cultured $2 \times 10^6$/well in 6 well plates.

Apoptotic Cells

Polymorphonuclear leukocyte (PMN) were allowed to undergo apoptosis by culture ex vivo in culture media. Jurkat cells were induced to undergo apoptosis by addition of staurosporine (1 µM) for 4 hrs.

Apoptotic Cell Co-Cultures

Macrophages were incubated with senescent neutrophils or apoptotic Jurkat cells (1:5 ratio) for 24 hrs. Senescent neutrophils were used as controls. Following co culture unbound cells were washed with PBS and attached macrophages were recovered and lysed by RIPA buffer.

Milk Preparation

Milk samples were obtained from dairy cows undergoing resolving or non-resolving $E$-$coli$ induced mastitis, or healthy cows. In order to separate the cellular and fat fraction from the aqueous fraction, samples were centrifuge at 1200 rpm for 5 minutes (cellular fraction), and the supernatants were transferred to 4° to solidify the fat fraction. After cooling overnight, the fat fraction was mechanically peeled from samples and the protein content in the soluble fraction was determined. Then, milk samples were added with sample buffer and run by SDS-PAGE. The cellular fraction was treated as the macrophage preparations described above.

Western Blot Analysis

Protein extracts were boiled prior to loading for 5 minutes in sample buffer, containing (for sample buffer ×2) 150 mM Tris pH 6.8, 20% glycerol, 4% SDS, 5% β-mercaptoethanol, and 15 ug/ml bromophenol blue. Equal amount of protein extracts from murine macrophages, bovine milk cells or bovine milk were run using 10% SDS-PAGE (5 μg/lane), transferred (1 h, 15V) to a nitrocellulose membranes (Biorad) blocked for 1 h with 5% BSA in TBST and immunoblotted over night at 40° C. with Rabbit anti-mouse/human lactoferrin (sc-25622, Santa Cruz Biotechnology, Inc.). Then, the membranes were washed 3 times with TBST, and incubated with the appropriate HRP-conjugated secondary antibody (1:10,000, 1 hr, room temperature, Jackson ImmunoResearch). The blots were washed and developed using EZ-ECL (Biological Industries) chemiluminescence kit and analyzed using the LAS-4000 luminescent image analyzer (FUJIFILM) and the TotalLab TL-100 software (Nonlinear Dynamics).

Interstitial Fluid Preparation from Lymphatic Organs

Inguinal and spleen lymph nodes were harvested from mice 24 or 66 hrs post peritonitis initiation (n=9). The organs were mechanically dissociated and strained through a 100 μm nylon mesh (Beckton-Dickinson) to produce a single cell suspension, followed by separation of cells from interstitial fluids by centrifugation (1,200 RPM×5 minutes). Then, red blood cells (RBC) were lysed using lysis buffer (biological industry) and interstitial fluids were saved at −20° C. for further analysis.

Interstitial fluids were added with sample buffer (1:1), boiled as indicated above, and equal protein amounts were run by SDS-PAGE (7.5% or 10%, acrylamide with 1-3% SDS at 80V for 30 minutes for upper gel and 120V for 90 minutes for lower gel) and transferred to a PVDF membrane. The membrane was blocked with 5% BSA and probed with rabbit anti-human/mouse Lactoferrin polyclonal IgG (sc-25622, Santa Cruz Biotechnology, Inc., 1:200 dilution), followed by a matching secondary antibody conjugated with horseradish peroxidase (HRP, 1:20,000 dilution). Membranes were developed with EZ-ECL detection kit (Biological Industries, Beit Haemek) and analyzed using Luminescent Image Analyzer LAS-4000 (Fujifilm Corporation) and "Image Reader LAS-4000" software (Fujifilm Corporation). Densitometry analysis were performed using TotalLab TL100 (nonlinear dynamics) image analysis software.

Example 1

Lactoferrin is Processed by Macrophages Incubated with Apoptotic Neutrophils

During the resolution of inflammation, macrophages uptake apoptotic polymorphonuclear cells (PMN) and migrate to the lymphatics. The presence of lactoferrin was examined in macrophages following engulfment of apoptotic PMN. To this end, peritoneal mouse macrophages were recovered 66 hrs after zymosan A injection. Then, the macrophages were incubated with apoptotic Jurkat cells (control, lane 2) or apoptotic neutrophils (lane 4). Apoptotic neutrophils (lane 3) or macrophages not incubated with apoptotic cells (lane 1) were used as controls as indicated. After incubation, cell lysates were prepared and run by SDS-PAGE and Western blot for lactoferrin.

As depicted in FIG. 1, in murine macrophages, a lactoferrin fragment (50 kDa), rather than the full length protein, was detected. Without wishing to be bound by any theory or mechanism, the lactoferrin fragment was most likely acquired from apoptotic PMN previously taken up by these macrophages. Senescent PMN contain full length lactoferrin and when engulfed by macrophages transfer considerable amounts of it to the macrophages. Lactoferrin is not transcribed de novo by macrophages and processed following the encounter of apoptotic cells as evident from the incubation of macrophages with apoptotic Jurkat cells (lane 2 in FIG. 1). The reduction in the 50 kDa fragment level following macrophage incubation with apoptotic cells suggests that this fragment is released following the uptake of apoptotic neutrophils.

These results indicate that lactoferrin present in neutrophil secondary granules is retained in apoptotic neutrophils, acquired by macrophages that clear these neutrophils, and processed by proteolysis to smaller fragments during the resolution of inflammation.

Example 2

Figure 2A:
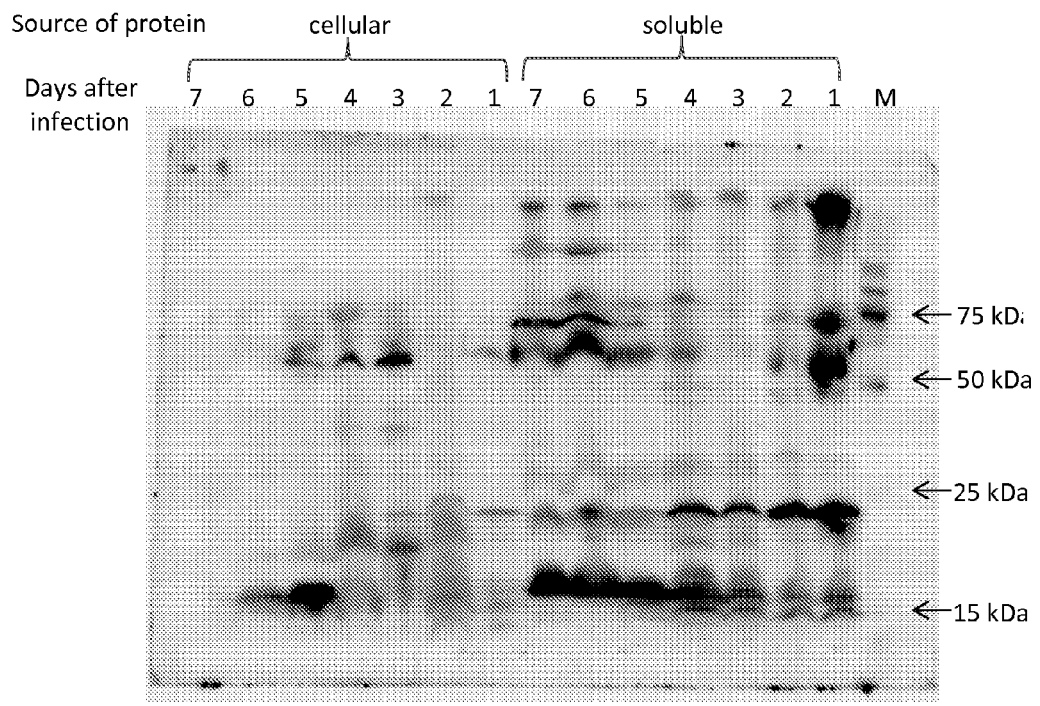
FIGS. 2A-2B Shows lactoferrin fragments obtained from milk of healthy or $E.\ coli$ infected cows.
Figure 2B:
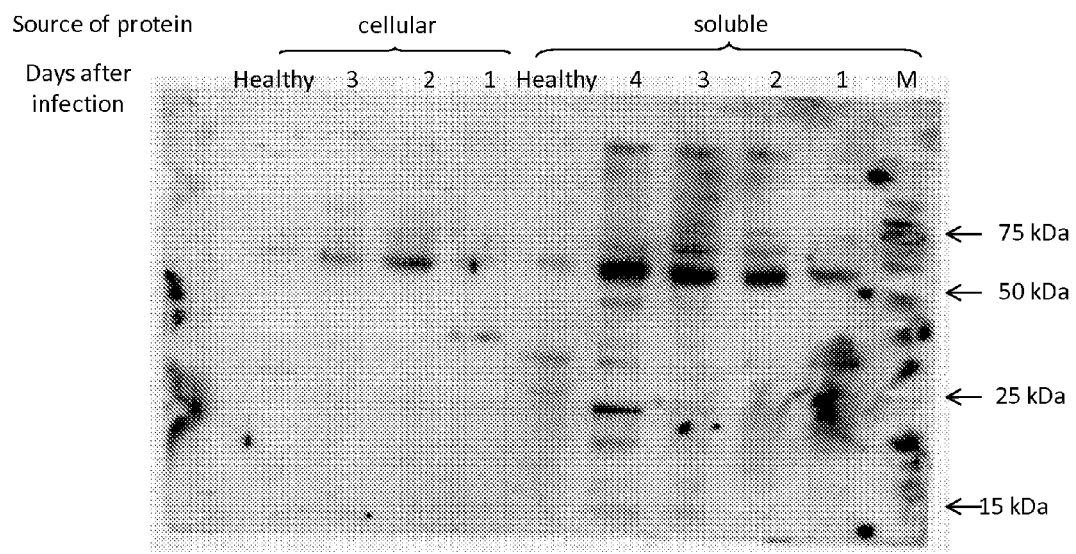
Figure 3A:
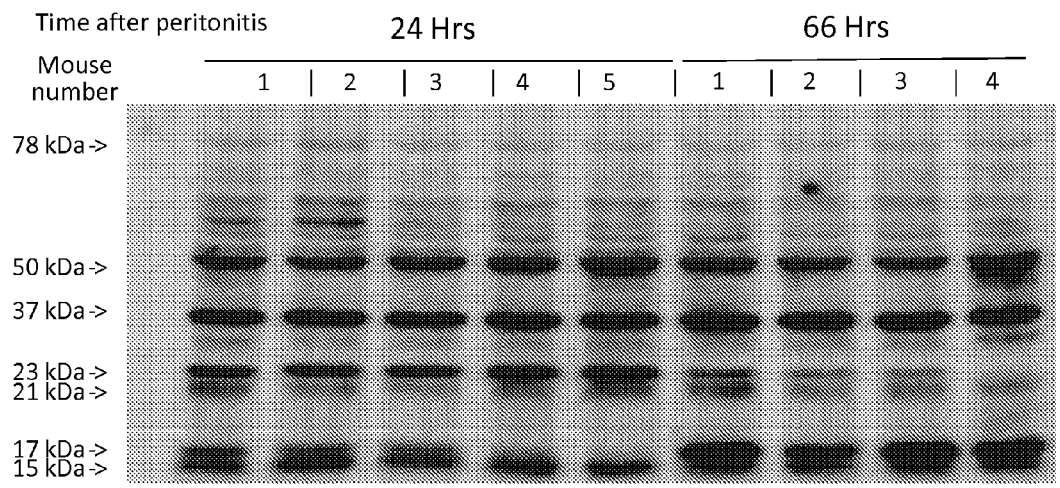
FIGS. 3A-3D Shows Lactoferrin fragments in interstitial fluids of spleen and inguinal lymph node during peritonitis. Spleen and inguinal lymph nodes were harvested 24 and 66 hrs after peritonitis initiation (n=9) and mashed. Equal amounts of interstitial fluid protein were run by 10% SDS PAGE, followed by Western blotting for Lactoferrin. The results demonstrate six different Lactoferrin-derived fragments: 50, 37, 23, 21, 17, and 15 kDa, in addition to the full length 78 kDa Lactoferrin. Results of representative blots from spleen and inguinal lymph nodes (A, C respectively) and average densitometric analysis (B, D respectively) are shown. * p value<0.05,  p value<0.005, * p value<0.001.
Figure 3B:
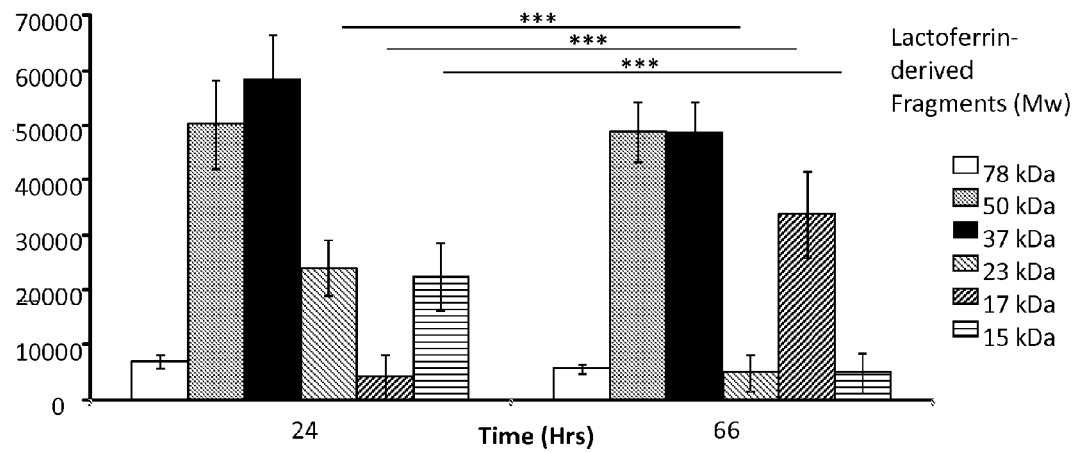
Figure 3C:
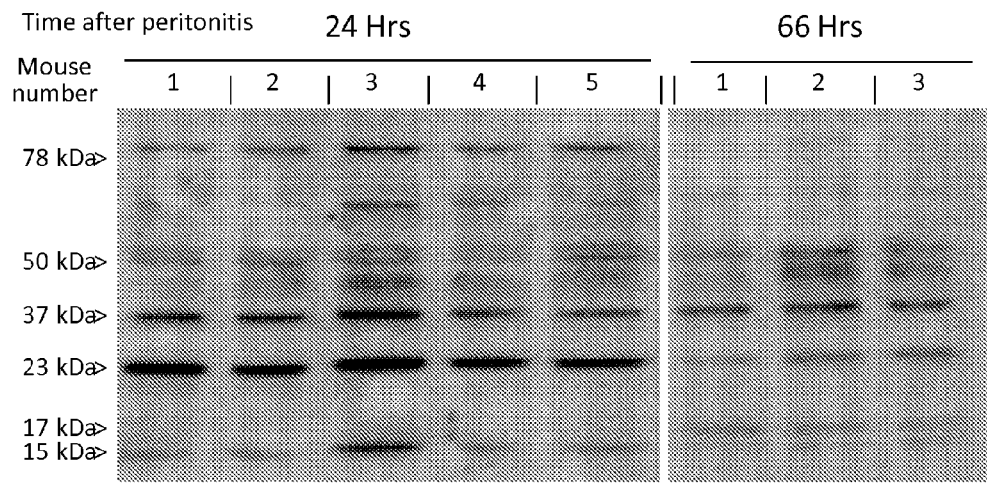
Figure 3D:
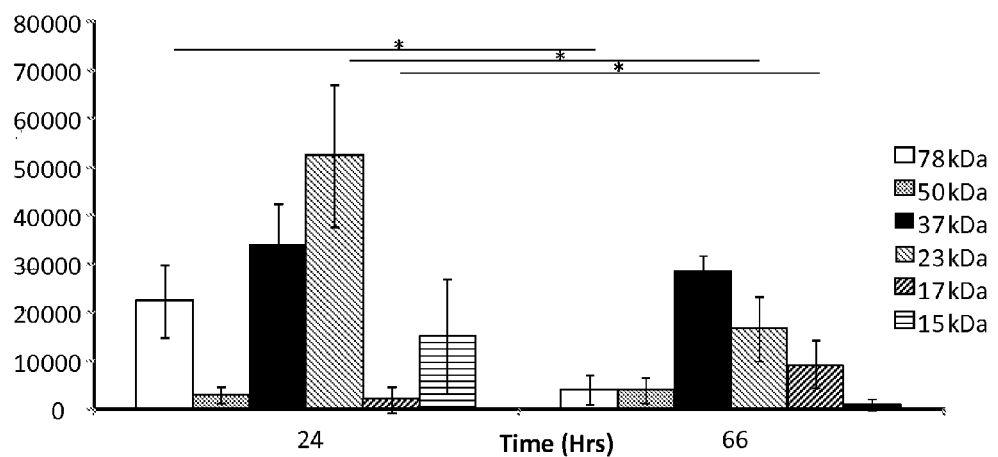

Lactoferrin Fragments Present During Inflammation and Resolution in Bovine Mastitis To determine whether lactoferrin fragments can be found in body fluids during the resolution of inflammation, milk samples from dairy cows that developed mastitis following infection with *E. coli* (FIG. 2A) were analyzed. Cows that did not clear the infection or healthy cows were used as controls (FIG. 2B).

The results indicate changes in the levels of several lactoferrin fragments during the inflammation-resolution switch. At days 1-3, a reduction in the amounts of the 75 and 55 kDa fragments was observed, wherein these fragments reappeared on days 4-7. The levels of the 23 and 15 kDa fragments reduced continuously on days 1-7, and the amounts of the 17 kDa fragment increased continuously between days 2-7. Most lactoferrin fragments were found in the cellular fraction of the milk and followed a similar but forward-pulled kinetics to the levels in the soluble fraction.

In non-resolving mastitis, a continuous increase in the levels of the 50 kDa fragment was observed, with a very late appearance of the 23 kDa fragment, and very low levels of the smaller fragments. In milk obtained from healthy cows, lactoferrin was barely detectable (at fragment sizes of 50, 30, and 25 kDa).

Thus the results indicate that the levels of lactoferrin fragments may be used to monitor the progress and fate of inflammation, and that the ratio between lactoferrin fragments of 23 and 17 kDa can be used as a diagnostic marker for transition from inflammation to resolution.

Example 3

Lactoferrin Fragments are Released to the Interstitial Space in Spleen and Inguinal Lymph Nodes During Inflammation and Resolution in Murine Peritonitis Since macrophages migrate to lymphoid organs during the resolution of inflammation, the inventors sought to determine whether lactoferrin fragments can be found in soluble forms at lymphoid organs, and whether their amounts change upon the shift from inflammation to resolution. To do so spleen and inguinal lymph nodes were harvested at two time periods (24 and 66 hrs) after peritonitis initiation and their interstitial fluids were assessed for Lactoferrin fragments content.

The results indicate that different amounts of several Lactoferrin cleavage products can be detected at 24 and 66 hrs post peritonitis initiation at the spleen and inguinal lymph nodes (LN; FIG. 3). The cleaved products of lactoferrin are similar in their molecular weight in either organ, and can be roughly defined as six distinguishable fragments of 50, 37, 23, 21, 17 and 15 kDa (as evaluated by SDS-PAGE), in addition to the full length 78 kDa protein. Significant differences were detected between spleen and inguinal LN during inflammation (24 hrs) and its resolution (66 hrs). There is a significant reduction in the amount of the 23 and 15 kDa fragments (5 fold and 4 fold, respectively) in the spleen, whereas an increase in the amount of the 21 and 17 kDa fragments (11 fold and 8 fold, respectively) can be detected (FIG. 3, A-B). In the inguinal LN however, a significant reduction in the amount of the 78, 23 and 15 kDa fragments (5 fold, 3 fold and 16 fold, respectively) could be noticed and an increase in the amount of the 17 kDa fragment (5 fold) is observed (FIG. 3, C-D). Thus, the amounts of different Lactoferrin fragments in the interstitial fluids from the spleen and inguinal LN change as inflammation resolves.

It can further be observed that the 17 kDa fragment can be identified as a common marker for resolving inflammation, since the amount of this fragment consistently increased during the transit from inflammation to resolution in both spleen and LN.

Example 4

Isolation of Bovine Lactoferrin and its Derived Fragments from Mastitis-Inflicted Cows Bovine lactoferrin was purified from mastitis-inflicted milk samples collected at day 3 or day 5 from the onset of infection. Milk samples were defatted by centrifugation at 2000 g for 30 min at 4° C., followed by mechanically scarping of the upper fat layer. The pH of the skim milk was adjusted to 4.6 with 5 N HCl and then centrifuged at 10,000 g for 1 hr to remove the casein precipitate. The whey was passed through a 0.45 mm filter to completely remove the casein precipitate and its pH was readjusted to 6.0 with 1N NaOH. The immunoglobulin in the whey was removed by ammonium sulfate precipitation (48%) for 30 min rotation in room temperature followed by 10,000 g centrifugation for 30 min. The solution in the whey was then replaced with 0.005 M sodium phosphate buffer (pH 6.0) using a 12-14 kDa cutoff membrane dialysis bag. Then, the samples were loaded onto a heparin affinity column and eluted by 3 step elution with 0.005 M sodium phosphate buffer (pH 6.0) containing 0.1, 0.3 or 0.5 M NaCl. The flowthrough was collected and lactoferrin-derived products were assessed by SDS-PAGE and Western blotting.

Figure 4A:
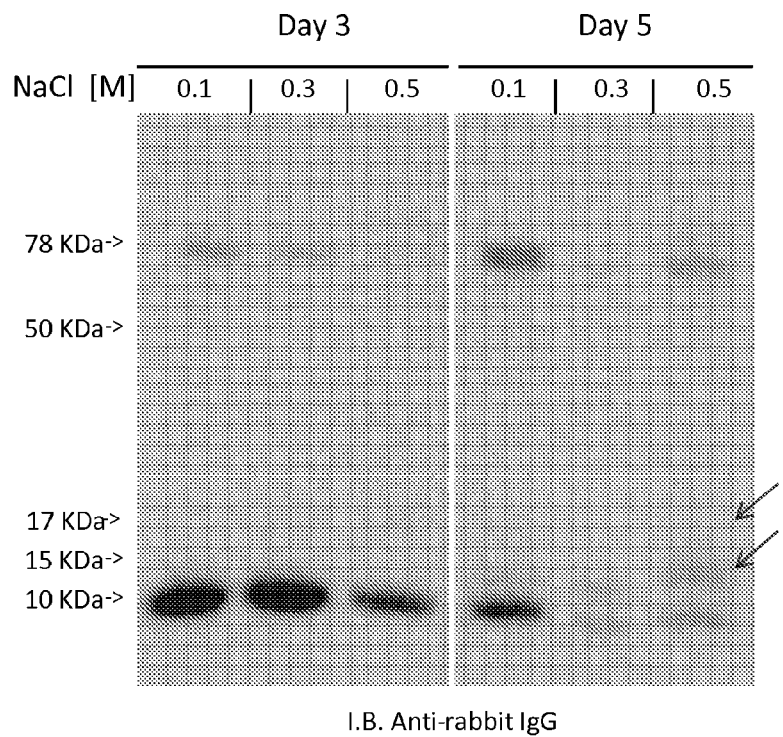
FIGS. 4A-4B Shows isolation of bovine Lactoferrin and its derived fragments from mastitis-inflicted cows. Milk samples were collected at day 3 (left) or day 5 (right) from the onset of infection and protein samples were eluted from a heparin affinity column at the indicated salt concentrations. Products were assessed by SDS-PAGE and Western blotting using secondary antibody only (FIG. 4A) or anti-lactoferrin sera and secondary antibody (FIG. 4B). Arrows indicate the locations of the 15 and 17 kDa lactoferrin fragments isolated from the gel following electrophoresis and subjected to sequencing.
Figure 4B:
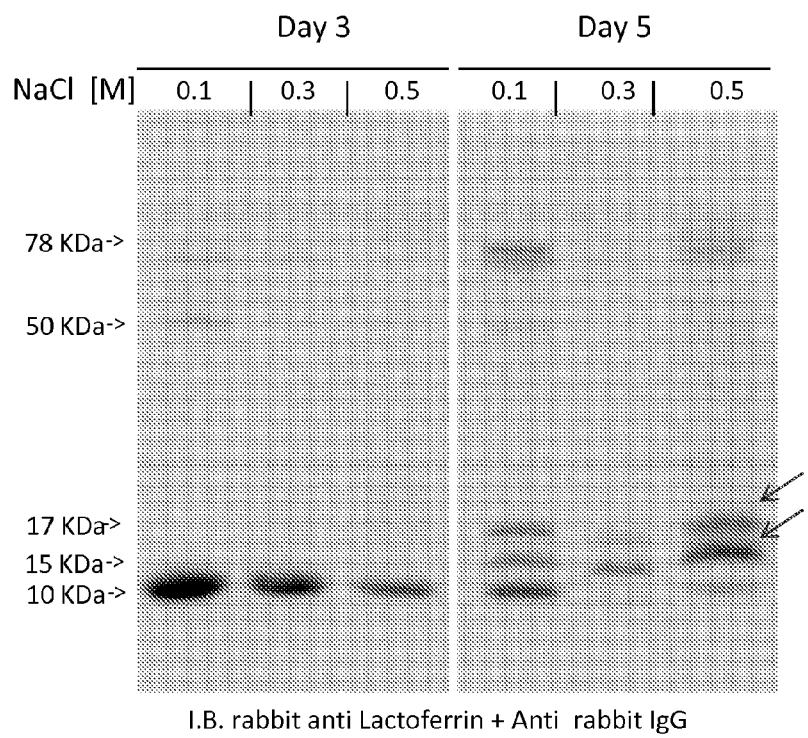

The results are presented in FIG. 4, showing molecular weight assessment of the resulting isolated fragments by SDS-PAGE and Western blotting using secondary antibody only (FIG. 4A) or anti-lactoferrin sera and secondary antibody (FIG. 4B). As can be seen in FIG. 4B a fragment of about 15 kDa may be detected at day 3, and decreases in amount by day 5. A fragment of about 17 kDa appears at day 5.

The fragments evaluated as being about 15 and 17 kDa following gel electrophoresis (day 5, 0.5M NaCl) were isolated from the gel, and subjected to proteolytic cleavage by Trypsin and Liquid chromatography—tandem mass spectrometry (LC-MS/MS) on LTQ-orbitrapmass spectrometer. Proteomic sequence analysis was performed by discoverer software version 1.3 against bovine part of the nr database and against decoy databases to determine false discovery rate (FDR). High identification confidence refers to 0.01 FDR.

What is claimed is:

1. A method for detecting resolution of inflammation in a bovine subject suspected of having mastitis associated with *E. coli* infection, the method comprising:
    obtaining a milk sample from the subject;
    determining by an immunoassay, in a soluble fraction of the sample, the presence of a lactoferrin fragment characteristic of resolution consisting of SEQ ID NO: 1 and of a lactoferrin fragment consisting of SEQ ID NO: 3;
    quantifying the amounts of said lactoferrin fragments, and determining the ratio of the amount of the fragment consisting of SEQ ID NO: 1 to the amount of the fragment consisting of SEQ ID NO: 3;
    wherein a ratio of at least 3 indicates the resolution of inflammation in the subject.

2. The method of claim 1, wherein when resolution of inflammation is not indicated by the determined ratio, the subject is determined to be a candidate for treatment for mastitis.

3. The method of claim 2, wherein the treatment comprises an antibacterial drug.

4. The method of claim 1, wherein the presence of the lactoferrin fragment characteristic of resolution consisting of SEQ ID NO: 1 is determined using an antibody specific for SEQ ID NO: 1.

5. A method for detecting inflammation in resolution in a bovine subject suspected of having mastitis associated with an *E. coli* infection, the method comprising:
- obtaining a milk sample from the subject within 7 days of the onset of *E. coli* infection in the subject;
- determining by an immunoassay, in a soluble fraction of the sample, the presence of a lactoferrin fragment consisting of SEQ ID NO: 1, and of a lactoferrin fragment consisting of SEQ ID NO: 3;
- quantifying the amounts of said lactoferrin fragments; and
- determining the ratio of the amount of the lactoferrin fragment consisting of SEQ ID NO: 1 to the amount of the lactoferrin fragment consisting of SEQ ID NO: 3;
- wherein a ratio of at least 3 indicates that said subject has inflammation in resolution in the subject.

* * * * *